Figure 1A:
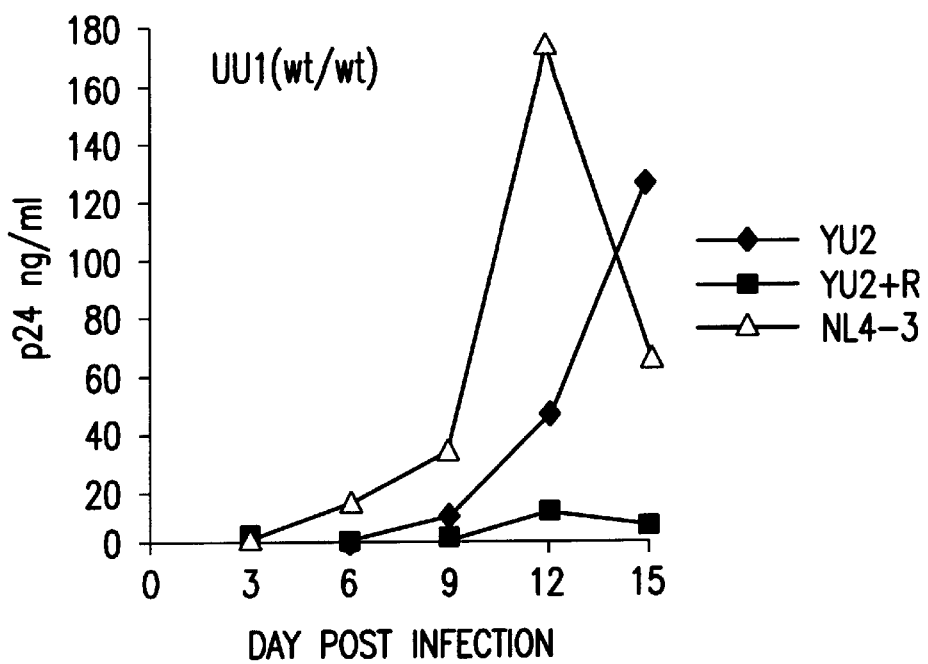

US006153431A

United States Patent [19]
Beretta et al.

[11] Patent Number: 6,153,431
[45] Date of Patent: Nov. 28, 2000

[54] HUMAN IMMUNODEFICIENCY VIRUS CO-RECEPTOR VARIANTS ASSOCIATED WITH RESISTANCE TO VIRUS INFECTION

[76] Inventors: Alberto Beretta, 3 avenue R. Schumann, Paris, 75007; Caroline Quillent, 33 rue Clément Perrot, Vitry-sur-Seine 94400; Fernando Arenzana Siesdedos, 18 rue de Rushemoor, Meudon 92190; Joséphine Braun, 5 place du Marché Ste Catherine, Paris, 75004, all of France

[21] Appl. No.: 09/087,232

[22] Filed: May 28, 1998

Related U.S. Application Data

[60] Provisional application No. 60/048,057, May 30, 1997.
[51] Int. Cl.[7] .............................. C12N 5/10; C07H 21/04
[52] U.S. Cl. ..................... 435/372.3; 435/455; 435/325; 435/354; 435/366; 435/372; 435/320.1; 536/23.4; 536/23.5
[58] Field of Search ................................. 435/320.1, 455, 435/325, 354, 366, 372, 372.3; 536/23.5, 23.4

[56] References Cited

PUBLICATIONS

Quillent et al., *Lancet* 351:14–18, Jan. 3, 1998.
Benkirane et al., Dec. 1997, "Mechanism of transdominant inhibition of CCR5–mediated HIV–1 infection by ccr5Δ32", J. Biol. Chem. 272:30603–30606.
Alkhatib et al., Jun. 1996, "CC CKR5: A RANTES, MIP–1α, MIP–1β receptor as a fusion cofactor for macrophage–tropic HIV–1", Science 272:1955–1958.
Choe et al., Jun. 1996, "The β–chemokine receptors CCR3 and CCR5 facilitate infection by primary HIV–1 isolates" Cell 85:1135–1148.
Dean et al., Sep. 1996, "Genetic restriction of HIV–1 infection and progression to AIDS by a deletion allele of the CKR5 structural gene" Science 273:1856–1862.
Deng et al., Jun. 1996, "Identification of a major co–receptor for primary isolates of HIV–1" Nature 381:661–666.
Doranz et al., Jun. 1996, "A dual–tropic primary HIV–1 isolate that uses fusin and the β–chemokine receptors CKR–5, CKR–3 and CKR–2b as fusion cofactors" Cell 85:1149–1158.
Dragic et al., Jun. 1996, "HIV–1 entry into CD4[+] cells is mediated by the chemokine receptor CC–CKR–5" Nature 381:667–673.
Liu et al., Aug. 1996, "Homozygous defect in HIV–1 coreceptor accounts for resistance of some multipy–exposed individuals to HIV–1 infection" Cell 86:367–377.
Samson et al., 1996, "Molecular cloning and functional expression of a new human cc–chemokine receptor gene" Biochemistry 35:3362–3367.
Samson et al., Aug. 1996, "Resistance to HIV–1 infection in caucasian individuals bearing mutant alleles of the CCR–5 chemokine receptor gene" Nature 382:722–725.
Cocchi et al., Dec. 1995, "Identification of RANTES, MIP–1α, and MIP–1β as the major HIV–suppressive factors produced by CD8[+] cells" Science 270:1811–1815.

*Primary Examiner*—Robert D. Budens

[57] ABSTRACT

The present invention relates to variants of the CCR5 human immunodeficiency virus ("HIV") co-receptor which result in a resistance of CCR5 expressing cells to HIV infection. The detection of such mutations may be used to identify individuals at lower risk for infection relative to the general population who, if infected, may exhibit slower progression to AIDS. Further, the present invention provides for methods of inhibiting HIV infection of a cell expressing the CCR5 receptor, comprising introducing, into the cell, a nucleic acid encoding a CCR5 variant.

13 Claims, 12 Drawing Sheets

```
N     T     M     C     Q     L     L
aat   aca   atg   tgt   caa   ctc   ttg...   WT
                  Hinc II N     T     M     Z     Q     L     L
aat   aca   atg   tga   caa   ctc   ttg...   M303
            ABSENCE OF Hinc II
```

FIG. 3A

Hinc II digestion

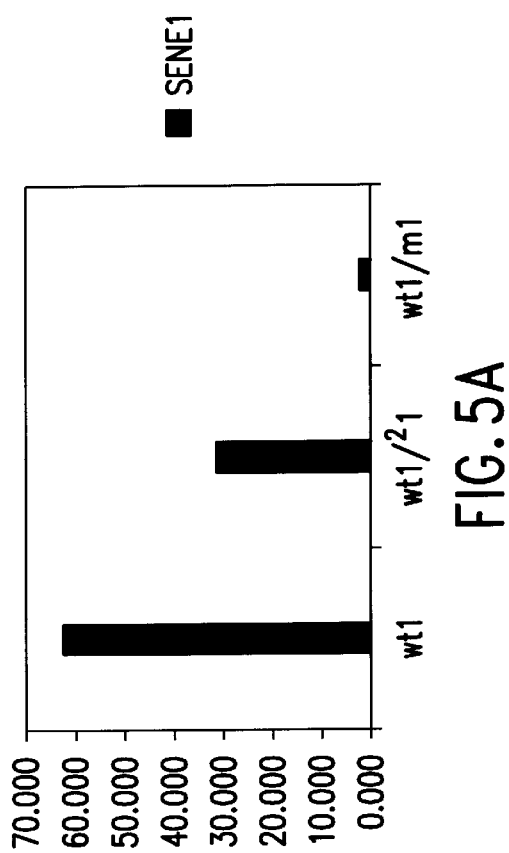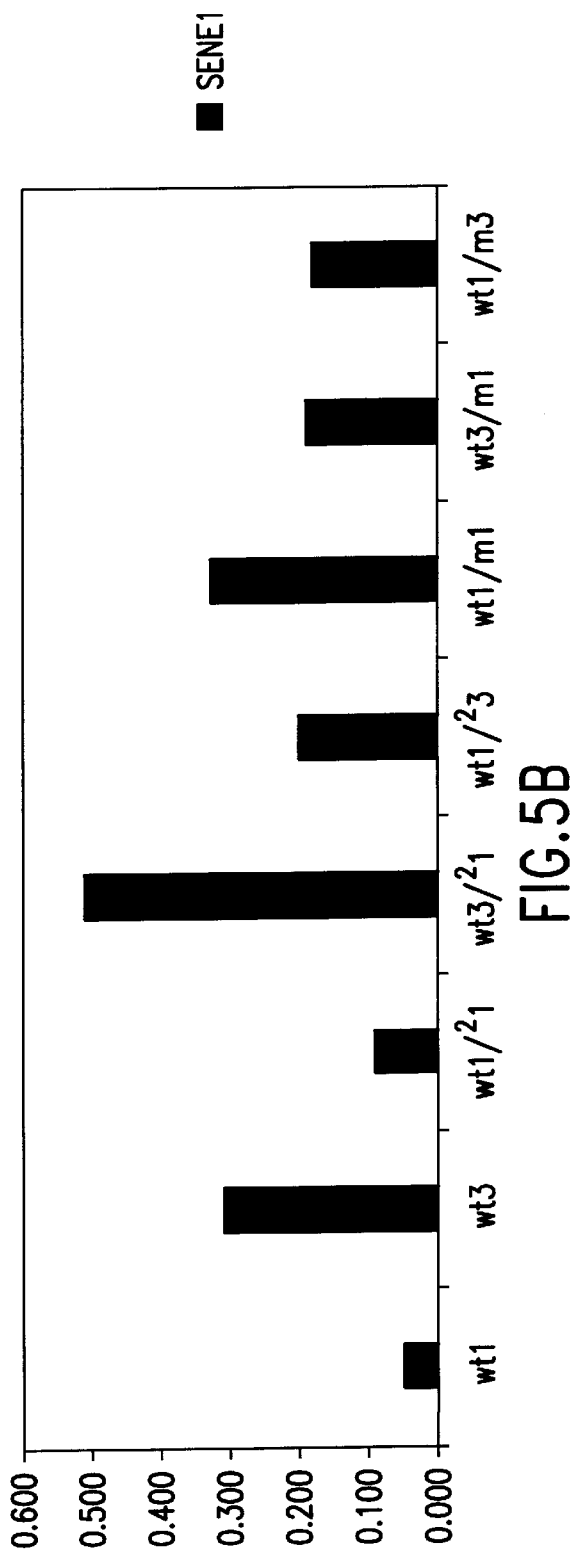
FIG. 5A
FIG. 5B

```
a      1376 b.p.     gaattcccccaa ... tgggctgggggt     linear
                                              Pnu4R I
                                              Hbv I
                      PflM I           Rma I  Nhe I
                      BsiY I                  Alu I
 EcoRI        Alu I    |   Rma I       |     III  |
   |            |      |     |         |      |   |
gaattcccccaacagagccaagctctccatctagtggacagggaagctagcagcaaaccttcccttcactacaaaacttc 80
cttaaggggggttgtctcggttcgagaggtagatcacctgtcccttcgatcgtcgtttggaagggaagtgatgttttgaag
   |            |      *|    |   *|           III  |
   1           21     31                       45
                       27                      46
                       27                      47
                                               50
                                               50

Hae III
      Msc I
      Hae I
      Eae I
      Tth111 II       Mse I    Acc I          Mse I
         |  ||          |        |              |
attgcttggccaaaaagagagttaattcaatgtagacatctatgtaggcaattaaaaacctattgatgtataaaacagtt 160
taacgaaccggttttttctctcaattaagttacatctgtagatacatccgttaattttttggataactacatattttgtcaa
         |  ||          |         |            |
         83            102       112           132
         87
         87
         87
         88

Sau3A I
                                                Mbo I
       Nla III                                  Dpn II
   Bsm I   MnI I    54           Rma I          Dpn I              Dra III       +53
    |   |   |       |              |              |                  |           ↑
tgcattcatggagggcaactaaatacattctaggactttataaaagatcacttttttatttatgcacagggtggaacaaga 240
acgtaagtacctcccgttgatttatgtaagatcctgaaatattttctagtgaaaaataaatacgtgtcccaccttgttct
    |   |   *|      |              |              |                  |
   162     171     190            206            224
           167                    206
                                  206
                                  206

Bsp1286 I
                                                         Ban II
                                                         Nla IV
       ↑                                                  | |
tggattatcaagtgtcaagtccaatctatgacatcaattattatacatcggagccctgccaaaaaatcaatgtgaagcaa 320
acctaatagttcacagttcaggttagatactgtagttaataatatgtagcctcgggacggttttttagttacacttcgtt
                                                          | |
                                                         290
                                                         291
                                                         291
```

FIG. 6A

```
                                                              Nla III
       Fau I                                                  NspC I                Fok I
       Fnu4H I                                                Nsp7524 I     Mnl I
       Ebv I   Mnl I   Mnl I              Ber I               Nsp I         Fok I
       |   |   |       |                  |                   | |           |  |  |
       atcgcagcccgcctcctgcctccgctctactcactggtgttcatctttggttttgtgggcaacatgctggtcatcctcat 400
       tagcgtcgggcggaggacggaggcgagatgagtgaccacaagtagaaaccaaaacacccgttgtacgaccagtaggagta
       |   |   |    •  |                  |                    •    ||       •   |  |  |
       324 332 339     353                                    382           392
       324                                                    382               395
           328                                                382                     398
                                                                  383

Hae III
                                                                 Msc I
                                                                 Hae I
                                                                 Hae I
                                                                 SerF I
                                      Nla III                    EcoR II
                               Mbo II                            Dsa V
                               Ear I                             BstN I
                               Eco57 I               BspM I      BstX X
                               |   |      |          |           | | |
       cctgataaaactgcaaaaggctgaagagcatgactgacatctacctgctcaacctggccatctctgacctgttttttccttc 480
       ggactatttgacgttttccgacttctcgtactgactgtagatggacgagttggaccggtagagactggacaaaaaggaag
       |   |         |    •  |                  |   •     |   ||
       420                                      442       452
           422                                            452
           422                                            452
                           428                            452
                                                          452
                                                              454
                                                              454
                                                              454
                                                                  455

Xcm I
                                            BsiY I
                       BspW I               Fnu4H I
                       Bsp1286 I            Fnu4H I                           Bsp1286 I
              BsiV I   Ban II      Bbv I    Bsr I                  Hinc II    Ban II
              |        |  |        |  ||    |                      |          |
       ttactgtcgggttctgggctcactatgctgccgcccagtggggactttggaaatacaatgtgtcaactcttcacagggctc 560
       aatgacagggggaagacccgagtgatacgacggcgggtcaccctgaaacctttatgttacacagttgagaactgtcccgag
       |   ||         |  ||         •  |      •                  •|      |          |
       488     496        507  515                                541          555
               496        507                                                  555
                          498       510
                                    511
                                    515
```

HUMAN IMMUNODEFICIENCY VIRUS CO-RECEPTOR VARIANTS ASSOCIATED WITH RESISTANCE TO VIRUS INFECTION

This application claims priority to U.S. Provisional Application Ser. No. 60/048,057, filed May 30, 1997.

1. INTRODUCTION

The present invention relates to variants of the CCR5 human immunodeficiency virus type-1 ("HIV-1") co-receptor which result in a resistance of CCR5-expressing cells to HIV-1 infection. The detection of such mutations may be used to identify individuals at lower risk for infection relative to the general population who, if infected, may exhibit slower progression to AIDS. Further, the present invention provides for methods of inhibiting HIV-1 infection of a cell expressing the CCR5 receptor, comprising introducing, into the cell, a nucleic acid encoding a CCR5 variant.

2. BACKGROUND OF THE INVENTION

Although human immunodeficiency virus type-1 ("HIV-1") uses the T cell surface molecule CD4 as a primary receptor, successful viral entry into and infection of a cell has been found to require the presence of a second molecule, or "co-receptor" (Clapham and Weiss, 1997, Nature 388:230–231). Seven co-receptor molecules have been identified, each of which are members of, or related to, the family of chemokine receptors, which are G-protein coupled receptors having seven transmembrane domains.

Chemokines are proteins having molecular weights from about 7–16 kDa which, acting as ligands at chemokine receptors, induce a rapid calcium influx and mediate a number of effects on the immune system (Murphy, 1996, Cytokine Growth Factor Rev. 7:47–64). Examples of chemokines include macrophage inflammatory protein ("MIP")-1a and MIP-1b, a protein which is regulated on activation normally _cell expressed and secreted ("RANTES"), monocyte chemoattractant protein ("MCP")-1, MCP-2, MCP-3, MCP-4, eotaxin, and stromal-derived factor ("SDF")-1 (Clapham and Weiss, 1997, Nature 388:230–231). Chemokines are proteins that are classified into two groups based on the presence of a non-cysteine amino acid ("X") between the first two ("CC") of four cysteine residues appearing in their amino acid sequence, giving rise to the CXC (cc) family and the CC (D) family. Receptors which specifically recognize CXC or CC chemokines are referred to, accordingly, as CXCR or CCR ("Dynamics of HIV Infection", Science and Medicine, March/April 1998: 36–45).

Two species of chemokine receptors which appear to be particularly relevant to HIV infection are CCR5 and CXCR4, for which the natural ligands are MIP-1a, MIP-1b and RANTES (CCR5) and SDF-1 (CXCR4). To date, most HIV-1 clinical isolates appear to use CCR5 or CXCR4, or both, as co-receptors with CD4 for entry into cells ("Dynamics of HIV Infection", Science and Medicine, March/April 1998: 36–45), and the presence of chemokine ligand inhibits infection via the corresponding receptor.

The cellular distributions of CCR5 and CXCR4 are associated with the role of these molecules in the course of HIV-1 infection. CCR5 (Samson et al., 1996, Biochemistry 35:3362–3367), which is mainly expressed on macrophages and memory T cells, serves as a co-receptor for infection by macrophage-tropic ("M-tropic") strains of HIV-1, which are found throughout the course of infection, are preferentially involved in sexual transmission of HIV-1, and are represented by non-syncytium-inducing laboratory isolates which do not cause cell/cell fusion in T cell lines ("Dynamics of HIV Infection", Science and Medicine, March/April 1998: 36–45; Cocchi et al., 1995, Science 270:1811–1815; Alkhatib et al., 1996, Science 272:1955–1958; Choe et al., 1996, Cell 85:1135–1148; Deng et al., 1996, Nature 381:661–666; Doranz et al., 1996, Cell 85:1149–1158; Dragic et al., 1996, Nature 381:667–673). CXCR4, however, which is expressed on a broader spectrum of cells, including naive T cells, serves as the co-receptor in late stages of infection for syncytium-inducing, T-cell-tropic ("T-tropic") strains of HIV-1 (Bleul et al., 1996, Nature 382: 829–833; Oberlin et al., 1996, Nature 382: 833–835; Feng et al., 1996, Science 272:872–877). Accordingly, the co-receptor which is more relevant to the initiation of HIV-1 infection appears to be CCR5.

Indeed, an association has been drawn between those rare individuals who remain persistently uninfected despite multiple sexual exposures to HIV and the presence of a 32 base pair deletion in the CCR5 gene ("CCR5Δ32"; Samson et al., 1996, Nature 382:722–725; Liu et al., 1996, Cell 86:367) which results in a frame shift mutation and the loss of the last three of the seven transmembrane domains (including the fifth, sixth and seventh transmembrane domains) present in the wild-type protein. Individuals heterozygous for this deletion, are, however, susceptible to infection (Dean et al., Science 273:1856), although progression to AIDS may be slowed (Dean et al., 1996, Science 273:1856–1862; Samson et al., 1996, Nature 382:722–725; Huang et al., 1996, Nature Med. 2:1240–1243; Michael et al., 1997, Nature Med. 3:338–340). It has been proposed (Benkirane et al., December 1997, J. Biol. Chem. 272:30603–30606) that co-expression of the CCR5Δ32 gene with the wild-type CCR5 gene results in trans-inhibition of the ability of CCR5 to act as an HIV co-receptor, in which the CCR5Δ32 protein interferes with dimerization of CCR5 at the cell surface. It has not, however, been confirmed that dimerization of CCR5 occurs or is necessary for viral entry.

3. SUMMARY OF THE INVENTION

The present invention relates to truncated variants of CCR5 which lack the portion of the molecule comprising the third to the seventh transmembrane domains. It is based, at least in part, on the discovery of a specific variant form of CCR5, termed "CCR5m303", in which the gene is mutated to create a stop codon which arrests translation before the third transmembrane domain. The presence of both CCR5m303 and CCR5Δ32 variant alleles in individuals was observed to confer resistance to infection by M-tropic strains of HIV-1.

The present invention is also based on the discovery that the CCR5m303 variant is more effective than CCR5Δ32 in trans-inhibiting the ability of wild-type CCR5 to act as a co-receptor for HIV. Therefore, individuals having a genotype which includes a wild-type CCR5 allele and a CCR5m303 variant allele may be protected against infection by M-tropic strains of HIV.

Accordingly, in a first series of embodiments, the present invention provides for compositions comprising a nucleic acid encoding the CCR5m303 variant and portions thereof which contain or which may be used to detect the m303 mutation.

In a second set of embodiments, the present invention provides for methods of identifying the presence of the CCR5m303 variant in an individual, wherein such methods may also include the identification of a second species of CCR5 variant. The presence of the CCR5m303 variant, in conjunction with wild-type CCR5 or a second species of CCR5 variant, bears a positive correlation with resistance to infection with M-tropic strains of HIV-1 and may be indicative of slower progression of disease in heterozygous individuals.

In a third set of embodiments, the present invention provides for compositions comprising a nucleic acid encoding a CCR5 variant which comprises the first two transmembrane domains found in wild-type CCR5 but lacks the remainder of the C-terminal end of the molecule, and for corresponding CCR5 variant proteins.

In a fourth set of embodiments, the present invention provides for methods of inhibiting CCR5-mediated HIV infection of a cell comprising decreasing the number of functional CCR5 molecules present at the surface of the cell. Such methods include, but are not limited to, introducing, into the cell, a nucleic acid encoding a CCR5 variant which comprises the first two transmembrane domains found in wild-type CCR5 but lacks the remainder of the C-terminal end of the molecule.

4. BRIEF DESCRIPTION OF THE DRAWINGS

FIGS. 1A–D. Infection of peripheral blood mononuclear cells ("PBMC") from two unexposed uninfected ("UU") and two exposed uninfected ("ExU") individuals with CCR5-dependent (YU2) and CXCR4-dependent (NL4-3) HIV molecular clones after inoculation with 20 ng p24/$10^6$ cells, with or without addition of RANTES (R). Results are expressed as the amount of p24 antigen in culture supernatants, and are representative of four independent experiments. CCR5 genotype for the Δ32 deletion is indicated in parenthesis (wt/wt)=homozygous wild type; (wt/Δ)=heterozygous Δ32; (Δ/Δ)=homozygous Δ32; and (wt?/Δ)=heterozygous Δ32 with an apparent wild type allele.

Figure 2:
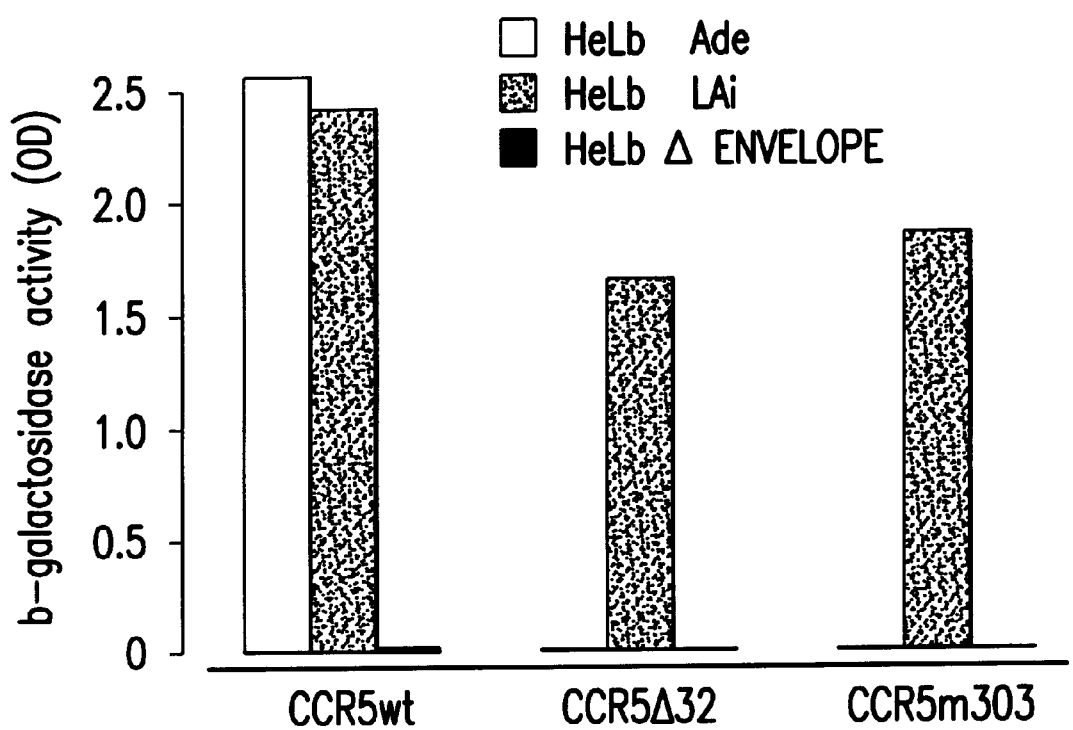

FIG. 2. Functional analysis of both CCR5 alleles cloned from ExU2 using an Env-mediated cell fusion assay.

FIGS. 3A–D. Genetic analysis of CCR5 from two UU individuals, two ExU individuals, and two siblings of ExU2. (A) DNA nucleotide and amino acid sequences of wild type (wt) and m303 alleles in a region spanning the 303 mutation (SEQ ID NOS: 5 and 6, respectively, where Z indicates a stop codon). (B) PCR amplification of genomic DNA using specific primers for the Δ32 deletion. (C) PCR amplification of the entire CCR5 gene from genomic (lanes 1–6) and plasmid (lanes 7–9) DNA, followed by (D), HincII digestion after amplification. A 1 kb DNA ladder was used as a marker. Genomic DNA following Δ32 PCR analysis is designated as follows: ExU2=exposed uninfected (m303/Δ32); 2.S=sister of ExU2 (wt?/Δ); 2.F=father of ExU2 (wt?/Δ); UU1=unexposed uninfected (wt/wt); ExU1=exposed uninfected (Δ32/Δ32); UU2=unexposed uninfected (wt/Δ); plasmid DNA corresponds to wild type (wt), Δ32, and m303 cloned alleles. wt?=apparent wild type allele.

Figure 4A:
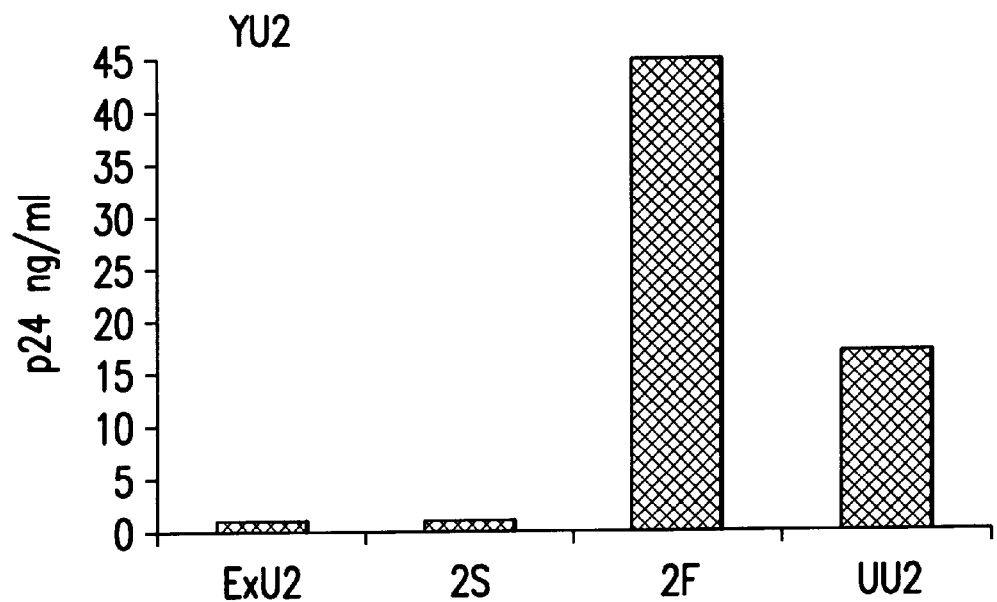
Figure 4B:
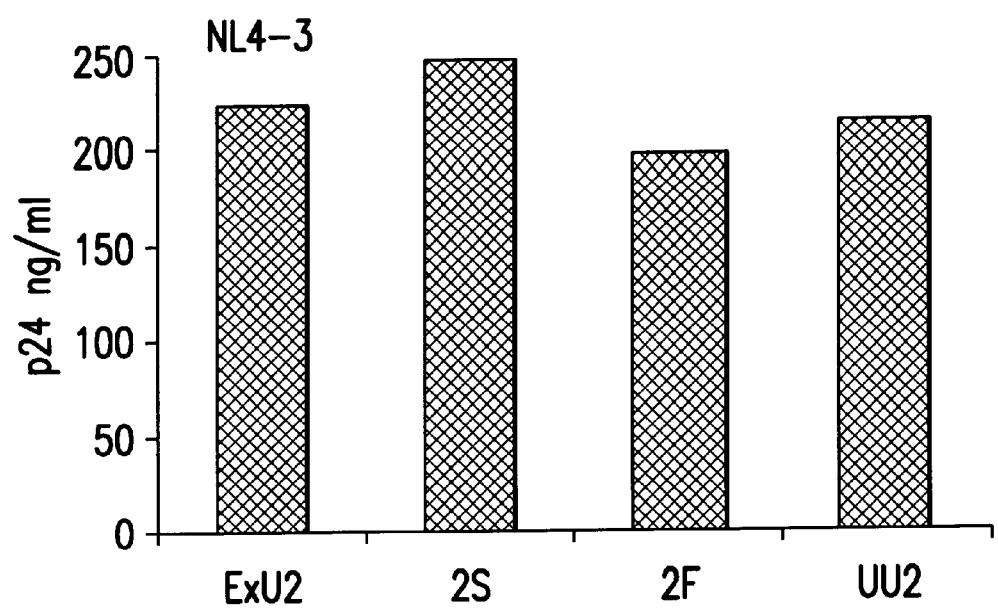

FIGS. 4A–B. Infection of PBMC from family members of ExU2 with CCR5-dependent (YU2) and CXCR4-dependent (NL4-3) viruses. Results are expressed as the amount of p24 antigen in cell-free culture supernatants. Day 12 of infection of PBMC from ExU2, 2.S, 2.F and UU2 with 0.5 ng p24/$10^6$ cells of (A) YU2 or (B) NL4-3 HIV molecular clones.

FIGS. 5A–B. Results of experiments studying transinhibitory effects of CCR5m303 as compared to CCR5Δ32. (A) beta-galactosidase expression in cell fusion assay; (B) CPRG lysis test following cell fusion assay.

Figure 6C:
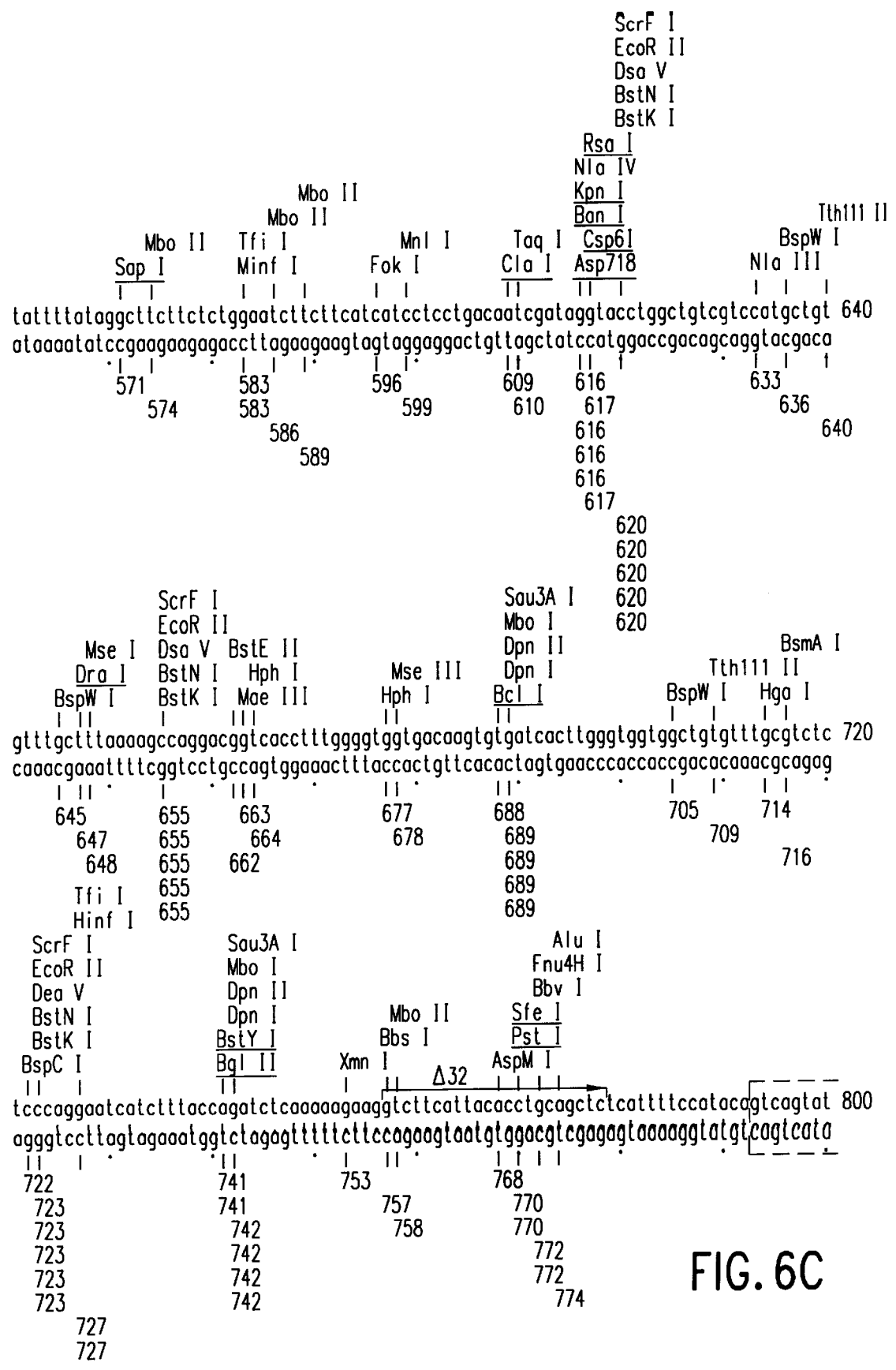
Figure 6D:
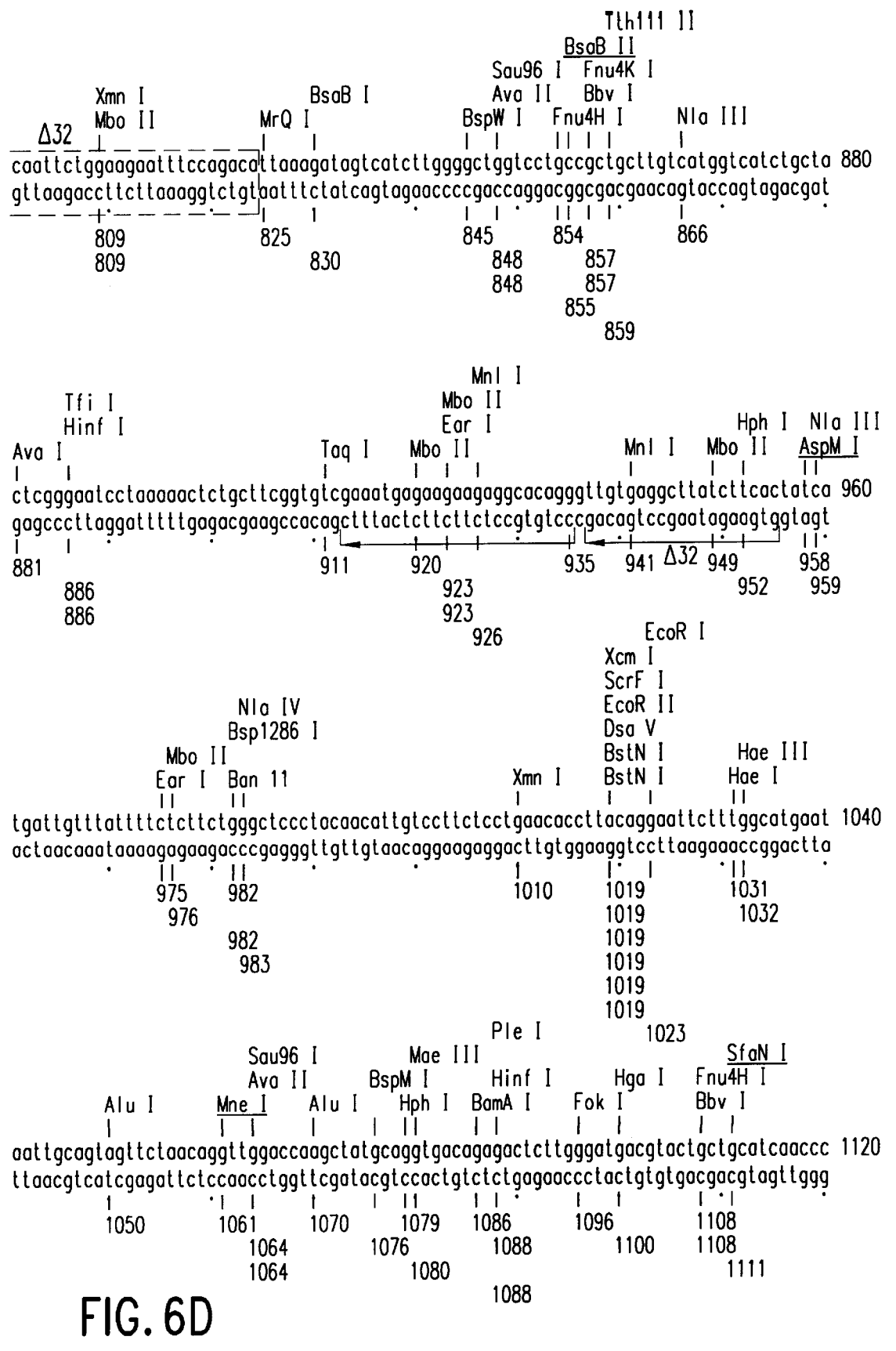
Figure 6E:
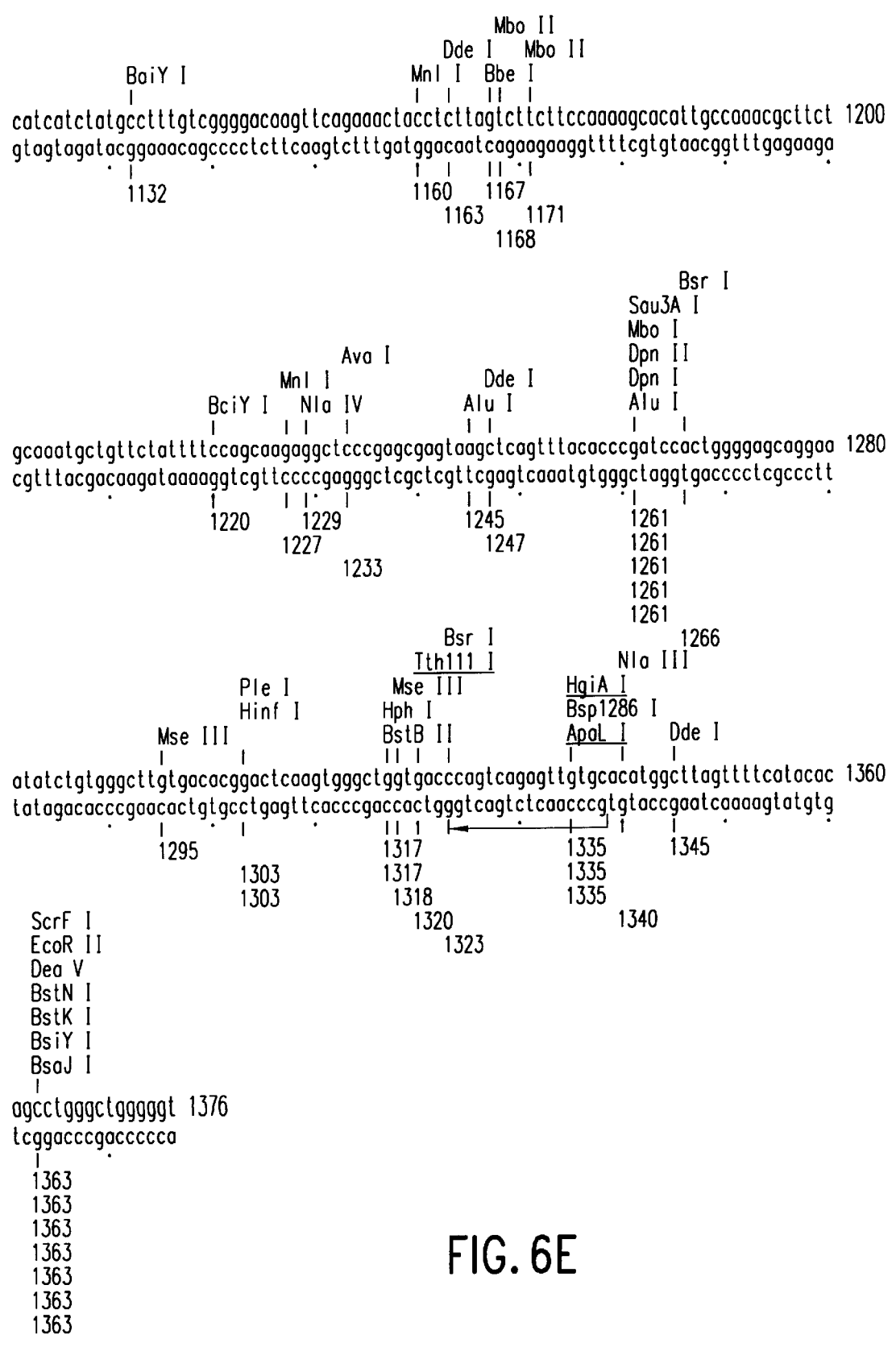

FIG. 6. Restriction map of the wild-type CCR5 gene.

5. DETAILED DESCRIPTION OF THE INVENTION

For clarity and not by way of limitation, the detailed description of the present invention is divided into the following subsections:

(i) CCR5 variants;

(ii) diagnostic utilities; and (iii) therapeutic utilities.

5.1. CCR5 Variants

The present invention relates to variants of CCR5 which comprise the first two transmembrane domains but lack the remainder of the C-terminal portion of the molecule. Such variants lack transmembrane domains 3–7 as found in wild-type CCR5.

With reference to the amino acid sequence of wild type human CCR5 (SEQ ID NO: 13), the present invention relates to CCR5 variants which comprise a portion having amino acid residues 1–87 of SEQ ID NO: 13 (this subsequence having SEQ ID NO: 18 and spanning the first two transmembrane domains of wild type CCR5), and which lack transmembrane domains 3 (residues 103–124 of SEQ ID NO: 13; SEQ ID NO: 19), 4 (residues 142–167 of SEQ ID NO: 13; SEQ ID NO: 20), 5 (residues 200–223 of SEQ ID NO: 13; SEQ ID NO: 21), 6 (residues 236–260 of SEQ ID NO: 13; SEQ ID NO: 22), and 7(residues 275–301 of SEQ ID NO: 13; SEQ ID NO: 23).

Accordingly, the present invention provides for a purified CCR5 variant protein which comprises the first two transmembrane domains (1 and 2) of wild-type CCR5 but which lacks transmembrane domains 3, 4, 5, 6 and 7. The CCR5 variant may further comprise additional heterologous amino acids as a fusion protein. The present invention also provides for nucleic acid molecules encoding such CCR5 variant proteins.

In particular nonlimiting embodiments, the present invention provides for a purified CCR5 variant protein which comprises a portion having the amino acid sequence set forth as SEQ ID NO: 18, but which does not contain amino acid sequences as set forth in SEQ ID NOS: 19–23. The present invention also provides for nucleic acid molecules encoding such CCR5 variant proteins. Such nucleic acids may themselves be truncated, or may comprise termination codons at positions 3' to the nucleotide residue at position 500 in SEQ ID NO: 12 (a full nucleic acid sequence of CCR5 is deposited in the Genbank/EMBL database, accession no. X91492).

In a specific nonlimiting embodiment, the present invention provides for a purified protein which is the CCR5 variant CCR5m303, which consists essentially of amino acid residues 1 –101 of SEQ ID NO: 13, CCR5m303 having a nucleic acid and amino acid sequence as set forth in SEQ ID NOS: 14 and 15, and for fusion proteins comprising the CCR5m303 variant joined to a heterologous protein sequence. The present invention also provides for purified and isolated nucleic acid molecules encoding such CCR5 variant proteins.

In other specific nonlimiting embodiments, the present invention provides for CCR5 variants consisting essentially of residues 1–88, 1–89, 1–90, 1–91, 1–92, 1–93, 1–94, 1–95, 1–96, 1–97, 1–98, 1–99, or 1–100, respectively, of the wild-type protein which has the sequence set forth in SEQ ID NOS: 12 and 13, or such proteins joined to a heterologous protein sequence in a fusion protein.

The proteins of the invention may be prepared by synthetic techniques, by cleavage of naturally derived CCR5, or, preferably, by recombinant technqiues.

The nucleic acids of the invention may be incorporated into suitable vectors for cloning and/or for expression, and, as such, may be operatively linked to appropriate promoter sequences, ribosome binding sequences, signal sequences, transciption termination sequences, polyadenylation sequences, splice donor/acceptor sequences, etc. Examples of such vectors include, but are not limited to, herpes simplex viral based vectors such as pHSV1 (Geller et al., 1990, Proc. Natl. Acad. Sci. U.S.A. 87:8950–8954); retroviral vectors such as MFG (Jaffee et al., 1993, Cancer Res. 53:2221–2226), and in particular Moloney retroviral vectors such as LN, LNSX, LNCX, LXSN (Miller and Rosman, 1989, Biotechniques 7:980–989); vaccinia viral vectors such as MVA (Sutter and Moss, 1992, Proc. Natl. Acad. Sci. U.S.A. 89:10847–10851); adenovirus vectors such as pJM17 (All et al., 1994, Gene Therapy 1:367–384; Berker, 1988, Biotechniques 6:616–624; Wand and Finer, 1996, Nature Medicine 2:714–716); adeno-associated virus vectors such as AAV/neo (Mura-Cacho et al., 1992, J. Immunother. 11:231–237); lentivirus vectors (Zufferey et al., 1997, Nature Biotechnology 15:871–875); baculovirus expression vectors such as p2Bac, and plasmid vectors such as pCDNA3 and pCDNA1 (InVitrogen), pET 11a, pET3a, pET11d, pET3d, pET22d, pET12a and pET28a (Novagen); plasmid AH5 (which contains the SV40 origin and the adenovirus major late promoter), pRC/CMV (InVitrogen), pCMU II (Paabo et al., 1986, EMBO J. 5:1921–1927), pZipNeo SV (Cepko et al., 1984, Cell 37:1053–1062), pSRa (DNAX, Palo Alto, Calif.) and pBK-CMV, pSPTg.T2FpAXK and pSPTg.2FXK (Schaleger et al., 1997, Proc. Natl. Acad. Sci. U.S.A. 94:3058–3063).

Suitable expression systems include mammalian cells, insect cells, yeast, bacteria, and plants.

The present invention also provides for a cell into which any of the foregoing nucleic acids has been introduced. The cell may be a vertebrate cell such as a mammalian cell (including, but not limited to, a human cell), a bacterial cell, a yeast cell, a plant cell, or an insect cell. The nucleic acid may be introduced by transfection, injection, electroporation, transformation, cell fusion, or any other standard technique.

The CCR5 variants of the invention either prevent or inhibit infection of a cell by a HIV virus which requires CCR5 as a co-receptor. The ability of the CCR5 variants to block or inhibit infection may be confirmed in a cell fusion assay such as the CD4+HeLa LTR/lacZ assay described in section 6 below.

5.2. Diagnostic Utilities

The present invention provides for a method of detecting the presence of a CCR5 variant which comprises the first two transmembrane domains (1 and 2) of wild-type CCR5 but which lacks transmembrane domains 3, 4, 5, 6 and 7 in an individual, wherein the presence of such a variant may bear a positive correlation with either a resistance to infection by M-tropic strains of HIV-1, a lower probability of infection or a slower progression of disease if such infection has occurred.

In particular, a determination that both CCR5 alleles of an individual encode a CCR5 variant which either (i) comprises the first two transmembrane domains of wild-type CCR5 but which lacks transmembrane domains 3, 4, 5, 6 and 7 or (ii) is functionally defective (e.g., cannot be expressed at the cell surface) has a positive correlation with a resistance of the individual to infection by M-tropic strains of HIV-1. One non-limiting example of a functionally defective CCR5 variant is the CCR5Δ32 variant.

Further, a determination that one CCR5 allele of an individual is a wild-type CCR5 allele and the other allele is a CCR variant which comprises the first two transmembrane domains of wild-type CCR5 but which lacks transmembrane domains 3, 4, 5, 6 and 7 may have a positive correlation with a decreased risk of infection, relative to homozygously wild-type individuals, and with slower progression of disease in the individual once infection with an M-tropic strain of HIV-1 has occurred. The phrase "slower progression of disease", as used herein, refers to a longer time interval between infection and progression to a diagnosis of acquired immunodeficiency syndrome (AIDS).

In preferred embodiments, the methods of the invention are directed toward detecting the presence of the CCR5m303 variant in an individual. Analogous methods may be used to detect the presence of other CCR5 variants as disclosed herein.

Non-limiting examples of genotypes having a positive correlation with resistance to infection to macrophage-tropic strains of HIV-1 would include individuals homozygous for CCR5m303, and individuals having one CCR5m303 allele and one CCR5Δ32 allele.

Non-limiting examples of genotypes which may have a positive correlation with a lower probability of infection with macrophage-tropic strains of HIV-1 or a slower progression of disease once infection had occurred would include individuals having one wild-type CCR5 allele and one CCR5m303 allele.

The presence of a CCR5 variant, as set forth above, or of wild-type CCR5, may be accomplished by detecting the presence of a nucleic acid or a protein which is characteristic of said variant or wild-type CCR5. Nucleic acid and amino acid sequences of wild-type CCR5 are set forth herein as SEQ ID NOS: 12 and 13. Nucleic acid and amino acid sequences of the CCR5m303 variant are set forth herein as SEQ ID NOS: 14 and 15. The CCR5Δ32 variant is characterized by the nucleic acid and amino acid sequences set forth in SEQ ID NOS: 16 and 17 (a nucleic acid sequence of the CCR5Δ32 variant is also deposited in the Genbank/EMBL database, assigned accession no. X99393), which has a deletion of nucleic acid residues 793–824 of the wild-type sequence (SEQ ID NO: 12 ).

Analysis may be performed using a suitable sample collected from the individual, including, but not limited to, a blood sample, and in particular a sample of PBMC.

The presence of the CCR5m303 variant, another CCR5 variant of the invention, or CCR5Δ32 variant in an individual may be detected by obtaining and characterizing (optionally sequencing) the CCR5 alleles of the individual, or portions thereof, for example portions spanning the 303 position or the Δ32 position (or other site of mutation), using standard techniques which preferably employ amplification technology. Using such technology, a biological sample collected from a subject to be tested is contacted with a pair of oligonucleotide CCR5-directed primers, under conditions which allow for the hybridization of the primers to nucleic acid template in the sample, the primers are extended under suitable conditions, dissociated from the template, and then re-annealed, extended, and dissociated such as to amplify the number of copies of CCR5 nucleic acid demarcated by the primers, and then the product of amplification may be characterized by electrophoresis, restriction endonuclease cleavage patterns, and/or nucleic acid sequencing using standard techniques.

In particular preferred non-limiting embodiments of the invention, the presence of the CCR5m303 allele in an individual may be detected by determining that a CCR5 allele in the individual lacks a HincII restriction enzyme cleavage site at the 303 position (see, for example, section 6, below). Nucleic acid encoding a CCR5 allele, prepared from a subject (e.g., from PBMC), may be tested for the presence or absence of this cleavage site, either directly, or, preferably, by amplification techniques. For example, the entire CCR5 gene sequence, or a portion thereof spanning the 303 mutation site, may be amplified using primers designed based on the sequence of the CCR5 gene (SEQ ID NO: 12). As nonlimiting examples, suitable primers may comprise between 15 and 100 nucleotides of sequence upstream or downstream of the nucleotide at position 540 of wild-type CCR5 (SEQ ID NO: 12). Specific nonlimiting examples of primers which amplify a fragment spanning the CCR5m303 (as well as the CCR5Δ32 mutation) mutation are TCC TTC TTA CTG TCC CCT TCT GG (SEQ ID NO: 7) and CCT GTG CCT CTT CTT CTC ATT TC (SEQ ID NO: 8).

In one nonlimiting specific example, for obtaining amplified DNA encoding the entire CCR5 gene, genomic DNA may be amplified using one of the following primer pairs: (i) primers: 5'-CCC AAG CTT ATG GAT TAT CAAGTG-3' (SEQ ID NO: 3) and 5'-GCT CTA GAT CAC AAG CCC ACA GA-3' (SEQ ID NO: 4) (see section 6, below); or (ii) primers 5' GGG CAA CTA AAT ACA T (SEQ ID NO: 5) and 5' GCA CAA CTC TGA CTG G (SEQ ID NO: 6). The restriction endonuclease HincII may then be added to amplified DNA prepared from the subject being tested (and preferably, in parallel, to a corresponding DNA sample representing the wild-type CCR5 gene), under conditions recommended by the enzyme manufacture for cleavage. The reaction product may then be separated to reveal restriction fragments, for example by electrophoresis in a 1 percent agarose gel. The absence of a HincII cleavage site at the 303 position is indicative of the presence of the CCR5m303 mutation. Where the entire CCR5 sequence is analyzed in this matter, the CCR5m303 mutation is associated with a single restriction fragment approximately 1.1 kb in size, compared with two fragments of approximately 0.7 and 0.3 kb in wild type and CCR5Δ32 alleles (the HincII site between the fragments evidently being eliminated by the mutation). Similar analysis regarding other CCR5 variants of the invention (lacking transmembrane domains 3–7) may be performed using the information found in the restriction map of the wild-type CCR5 gene shown in FIG. 6.

Identification of the presence of the CCR5Δ32 variant, in a specific non-limiting embodiment, may be performed using the primers 5'-GTC TTC ATT ACA CCT GCA GCT C-3' (SEQ ID NO: 1); primer 2: 5'-GTG AAG ATA AGC CTC ACA GCC-3' (SEQ ID NO: 2) and as set forth in section 6, below. Other suitable primers (for example, those having sequences as set forth in SEQ ID NOS: 7 and 8 and as described above) may be used, designed based on the region distinguishing the wild-type gene from that encoding the CCR5Δ32 variant. An example of the use of primers having sequences as set forth in SEQ ID NOS: 7 and 8 to distinguish between alleles based on amplified fragment size and HincII cleavability is set forth in Section 7 below.

Alternatively, CCR5 variants may be detected using oligonucleotide probes specific for regions of the CCR5 gene altered by mutation. For example, the oligonucleotide probe AATACAATGTGTCAACTCTTG (SEQ ID NO: 9) may be used to identify the wild-type gene, whereas the oligonucleotide AATACAATGTGACAACTCTTG (SEQ ID NO: 10) may be used to identify a gene containing the 303 mutation (for example using hybridization techniques, preferably under stringent conditions).

Therefore, in particular nonlimiting embodiments, the present invention provides for a method of detecting the presence of at least one CCR5 variant in a biological sample, comprising (i) bringing the biological sample into contact with a pair of primers selected from the group consisting of oligonucleotides having (a) SEQ ID NO: 1 and SEQ ID NO: 2; (b) SEQ ID NO: 3 and SEQ ID NO: 4; (c) SEQ ID NO: 5 and SEQ ID NO: 6; and (d) SEQ ID NO: 7 and SEQ ID NO: 8; (ii) amplifying a DNA fragment of the CCR5 variant using said primer pair; (iii) demonstrating the amplification of the DNA fragment corresponding to the fragment flanked by the primers, for example by gel electrophoresis; and, optionally (iv) verifying the sequence of the amplified fragment, for example by specific probe hybridization, sequencing, or restriction site analysis.

The present invention also provides for a method of rapid detection of the presence of two simultaneous variants of the CCR5 gene, wherein the first variant is a CCR5m303 variant and the second variant is the CCR5Δ32 variant, comprising bringing a biological sample into contact with a pair of primers having sequences as set forth in SEQ ID NOS: 7 and 8, and a step in which the product resulting from the interaction between the nucleotide sequence of the CCR5m303 allele and the CCR5Δ32 allele may be detected by any suitable means.

Identification of the foregoing variants may also be performed at the protein level, for example, by subjecting a protein sample collected from an individual and subjecting such protein to Western blot analysis, wherein an antibody directed against CCR5 is used to identify CCR5 proteins expressed in the individual. The appearance of a CCR5 protein having a molecular weight which is lower than wild-type (40.6 kDa), and preferably of about 10 kDa–14 kDa (the molecular weight of CCR5m303 being approximately 13.8 kDa), is indicative of the presence of a CCR5 variant having the characteristics set forth above.

As such, the present invention provides for molecules, compositions and kits which may be used in the foregoing analysis. Such molecules include but are not limited to oligonucleotide molecules which may be used to detect nucleotide defects in a CCR5 gene which give rise to the variants described above. Such oligonucleotides preferably have a length between 8 and 100 and more preferably between 20 and 50 bases in length, and may optionally be detectably labeled, for example, with a radioactive or a non-radioactive compound. Specific non-limiting embodiments are oligonucleotides comprising the sequences GTCTTCATTACACCTGCAGCTC (SEQ ID NO: 1); GTGAAGATAAGCCTCACAGCC (SEQ ID NO: 2);CCCAAGCTTATGGATTATCAAGTG (SEQ ID NO: 3); GCTCTAGATCACAAGCCCACAGA (SEQ ID NO: 4), GGGCAA CTA AATACAT (SEQ ID NO: 5); 5' GCACAACTCTGACTGG (SEQ ID NO: 6); TCCTTCTTACTGTCC CCT TCT GG (SEQ ID NO: 7) and CCTGTGCCTCTTCTT CTC ATT TC (SEQ ID NO: 8); wherein SEQ ID NOS: 1 and 2, and SEQ ID NOS: 7 and 8, are particularly useful in detecting the presence of CCR5Δ32 and SEQ ID NOS: 3 and 4 and SEQ ID NOS: 5 and 6 are useful in amplifying the entire CCR5 gene (wherein SEQ ID NOS: 5 and 6 may be particularly useful where the obtained fragment (containing the entire gene) is to be sequenced and SEQ ID NOS: 3 and 4 may be particularly useful when the fragment is to be cloned and sequenced because of the incorporation of restriction sites). The positions of these various primers relative to the CCR5 gene sequence (SEQ ID NO: 12) are as follows: SEQ ID NO: 1, position 757; SEQ ID NO: 2, position 955; SEQ ID NO: 3, position 240; SEQ ID NO: 4, position 1298; SEQ ID NO: 5, position 173; SEQ ID NO: 6, position 1338; SEQ ID NO: 7, position 475, and SEQ ID NO: 8, position 935. SEQ ID NO: 3 contains a restriction site for HindII. SEQ ID NO: 4 contains a restriction site for XbaI. Suitable kits for performing methods of the invention may comprise (i) a CCR5 oligonucleotide primer and (ii) a reagent for performing an amplification reaction therewith.

5.3. Therapeutic Utilities

Because it has been observed that the CCR5m303 variant has a trans-inhibitory effect on the ability of wild-type CCR5 to act as a suitable co-receptor for M-tropic strains of HIV-1, the present invention provides for methods of inhibiting infection of a CCR5-expressing cell comprising introducing, into the cell, a CCR5 variant which comprises the first two transmembrane domains (1 and 2) of wild-type CCR5 but which lacks transmembrane domains 3, 4, 5, 6 and 7. In preferred embodiments, the CCR5 variant is CCR5m303.

The CCR5 variant may be introduced into the cell by introducing, into the cell, a nucleic acid encoding the CCR5 variant, either by infection with a virus containing the CCR5-encoding nucleic acid (such as a retrovirus, adenovirus, adeno-associated virus, etc.) or by injection of nucleic acid into the cell or surrounding tissue. Such introduction may be accomplished when the cell is part of a subject to be treated (an in vivo approach) or when the cell has been removed from the subject (an ex vivo approach).

As a specific, non-limiting example, nucleic acid encoding the CCR5m303 variant may be introduced selectively into cells which are CCR5+ and CD4+. In further specific nonlimiting embodiments, expression of the nucleic acid encoding the CCR5 variant may be placed under the control of an inducible promoter or such that a trans-acting sequence is required (for example by an HIV-encoded factor such as tat), so that expression in the cell is not constitutive.

6. EXAMPLE: MUTATIONS OF CCR5 IN INDIVIDUALS EXPOSED TO BUT UNINFECTED BY HUMAN IMMUNODEFICIENCY VIRUS 6.1. Materials and Methods Determination of susceptibility of PBMC from UU or ExU individuals to infection, and of effects of RANTES on infection. Cultures of peripheral blood mononuclear cells ("PBMC") collected from two unexposed uninfected ("UU") and two exposed uninfected ("ExU") individuals were inoculated with either CCR5-dependent (YU2) or CXCR4-dependent (NL4-3) HIV molecular clones, using a virus inoculum of 20 ng p24/$10^6$ cells, with or without addition of RANTES (R), as follows. Ficoll purified human PBMC were activated by 1 $\mu$g/ml PHA-P (Glaxo Wellcome, Paris, France) for 72 hours in RPMI 1640 medium (Gibco/BRL Life Technologies, Cergy, France) containing 10 percent fetal calf serum ("FCS") and infected with HIV-I containing an amount of p24 antigen determined by ELISA (Dupont de Nemours, Wilmington, Del.) for 2 hours. Cells were washed three times with PBS and cultured at $10^6$ cells per ml in RPMI 1640 medium containing 10 percent FCS and 20 ng/ml recombinant interleukin 2 (rIL-2) (EuroCetus, France). Every three days the culture fluid was harvested and replaced with fresh medium containing rIL-2 and the amount of p24 antigen in the cell-free supernatants was measured by ELISA. Inhibition of infection by human recombinant RANTES (Biodesign International, Kennebunk, Me.) was performed by adding 125 nmol final concentration at the time of infection and each time the medium was replaced.

Functional analysis of both CCR5 alleles cloned from ExU2 using an Env-mediated cell fusion assay. A CD4+ HeLa (lacZ) cell clone was generated in HeLa cells carrying a stably integrated lacZ gene under HIV-I LTR control by stable transfection with a retroviral vector containing CD4 cDNA (P4 HeLa cell clone; Clavel and Cameau, 1994, J. Virol. 68:1179). Stable surface expression of the HIV-1 LAI envelope glycoprotein in human HeLa cells (HeLa LAI cells) was achieved by transfection of pMA243, an HIV-1 provirus (from M. Alizon) derived from an infectious HIV-1 LAI provirus in which the gag and pol genes are deleted and the nef gene is replaced by the dhfr drug resistance gene (Dragic et al., 1992, J. Virol. 68:4794). Stable surface expression of the HIV-1 Ada envelope glycoprotein in HeLa cells (HeLa Ada cells) was obtained by substituting the HIV-1 LAI envelope glycoprotein by the HIV-1 Ada envelope glycoprotein in pMA243 (Pleskoff et al., 1997, Science). HeLa cells lacking HIV-1 env expression (HeLa Δenv cells) were obtained by transfection of pMA273, an env-defective provirus (Dragic et al., 1992, J. Virol. 68:4794). CD4+ HeLa (LTR lacZ) cells were transiently transfected with PcDNA3-based constructs permitting the expression of either CCR5 wild type (CCR5wt), m303 (CCR5m303) or Δ32 (CCR5Δ32) cDNA. After 24 hours, cells were cocultured with HeLa Ada, HeLa LAI or HeLa Δenv cells. Cell fusion was evaluated after 24 hours by measuring β-galactosidase activity in cell lysates and assessed as described in Oberin et al., 1996, Nature 382:833.

Genetic analysis of CCR5 from two UU individuals, two ExU individuals, and two siblings of ExU2. The Δ32 fragment was amplified by PCR from PBMC genomic DNA using the following primers: primer 1: 5'-GTC TTC ATT ACA CCT GCA GCT C-3' (SEQ ID NO: 1); primer 2: 5'-GTG AAG ATA AGC CTC ACA GCC-3' (SEQ ID NO: 2). PCR was conducted with 1 $\mu$g of genomic DNA using 0.2 mM dNTPs, 0.2 $\mu$M primers, and 1.25 U of AmpliTaq Gold polymerase (PE Applied Biosystems, Branchburg, N.J.) for 35 cycles (94° C., 40 sec.; 60° C., 40 sec.; 72° C., 40 sec.) after an initial 10 minutes denaturation at 94° C. The resulting PCR products were separated on a 2 percent Nusieve agarose gel. Two fragments of 198 bp and 166 bp corresponding to the wild-type and the deleted CCR5 alleles were obtained. For cloning and sequencing of the entire CCR5 gene, genomic DNA was amplified using the following primers: primer 3: 5'-CCC AAG CTT ATG GAT TAT CAAGTG-3' (SEQ ID NO: 3); primer 4: 5'-GCT CTA GAT CAC AAG CCC ACA GA-3' (SEQ ID NO: 4). PCR of genomic and plasmid DNA (200 ng) was conducted as above for 30 cycles (94° C., 1 min. 30 sec.; 47° C., 1 min.; 72° C., 1 min. 30 sec.) after an initial 10 min denaturation at 94° C. The amplified products were cloned in a pCR3 vector using the TA cloning kit (Invitrogen, Leek, Netherlands). Automatic sequencing was performed using the same primers (ESGS, Research and Development department, Evry, France). For analysis of restriction enzyme products of different CCR5 alleles, the entire CCR5 cDNA was amplified using the same set of primers as above, digested with HincII, and the fragments separated on an agarose gel.

Infection of PBMC from family members of ExU2 with CCR5-dependent (YU2) and CXCR4-dependent (NL4-3) viruses. Ficoll purified PBMC were activated as above for four days and infected with 0.5 ng p24/$10^6$ cells of either YU2 or NL4-3 HIV molecular clones after 1 day in RPMI 1640 medium supplemented with 10 percent FCS, 1 U/ml anti-αIFN (Valbiotech, Paris, France) and 2 $\mu$g/ml polybrene (Sigma, France).

6.2. Results and Discussion

ExU1 and ExU2 are two Caucasian homosexual men who reported multiple incidents of unprotected sexual intercourse during the last ten years. ExU2 reported numerous sexual relationships with multiple partners who succumbed to AIDS and is now the stable partner of an HIV-infected person. No evidence of HIV-1 infection was detected in either ExU individual by standard techniques (HIV-1 ELISA and RNA PCR, Roche), nor was there evidence of clinical or immune alterations as determined by the CD4/CD8 ratio and other parameters of cellular immunity.

The CCR5 genotypes of ExU1 and ExU2 were first determined by PCR of genomic DNA using a pair of primers which allow amplification of the DNA fragment containing the Δ32 base pair deleted sequence of CCR5Δ32 (Liu et al., 1996, Cell 86:367). ExU1 was found to be homozygous for the deleted allele (Δ/Δ) while ExU2 displayed only one deleted allele (wt?/Δ; where wt? indicates that one allele of CCR5 in this individual lacked the 32 base pair deletion and was therefor presumed to be wild type).

There is evidence for an association between CCR5Δ32 homozygosity and resistance to infection (Samson et al., 1996, Nature 382:722; Liu et al., 1996, Cell 86:367) whereas the same deletion, when present as a heterozygous trait, does not confer resistance (Dean et al., 1996, Science 273:1856; Huang et al., 1996, Nature Med. _2:1240). Cells of CCR5Δ32 heterozygous individuals (like ExU2) are typically susceptible to infection by CCR5-dependent viruses (Samson et al., 1996, Nature 382:722).

To determine whether the presumably exposed but uninfected individuals were resistant to infection, PBMC from both individuals were tested for their ability to be infected by either of two molecular clones of HIV-1: YU2, which uses CCR5 as a co-receptor (Li et al., 1992, J. Virol. 66:6587), and NL4-3, which is strictly CXCR4-dependent (Zhang et al., 1996, Nature 383:768). PBMC from two uninfected unexposed (UU) individuals, who were either homozygous (wt/wt) for the wild type CCR5 allele (UU1) or heterozygous (wt/Δ) for the deleted allele (UU2) were used as controls.

Figure 1B:
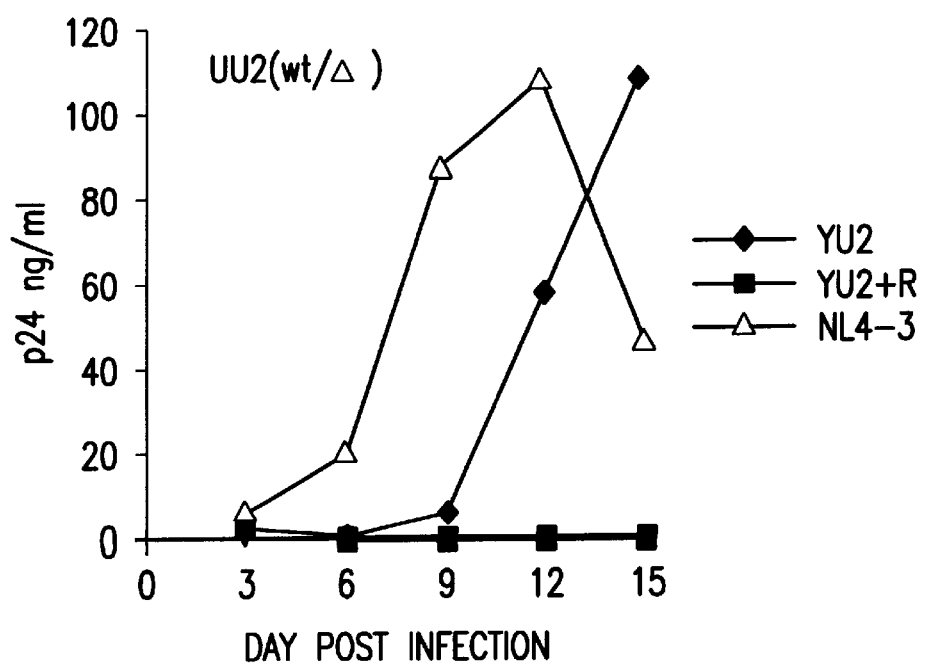
Figure 1C:
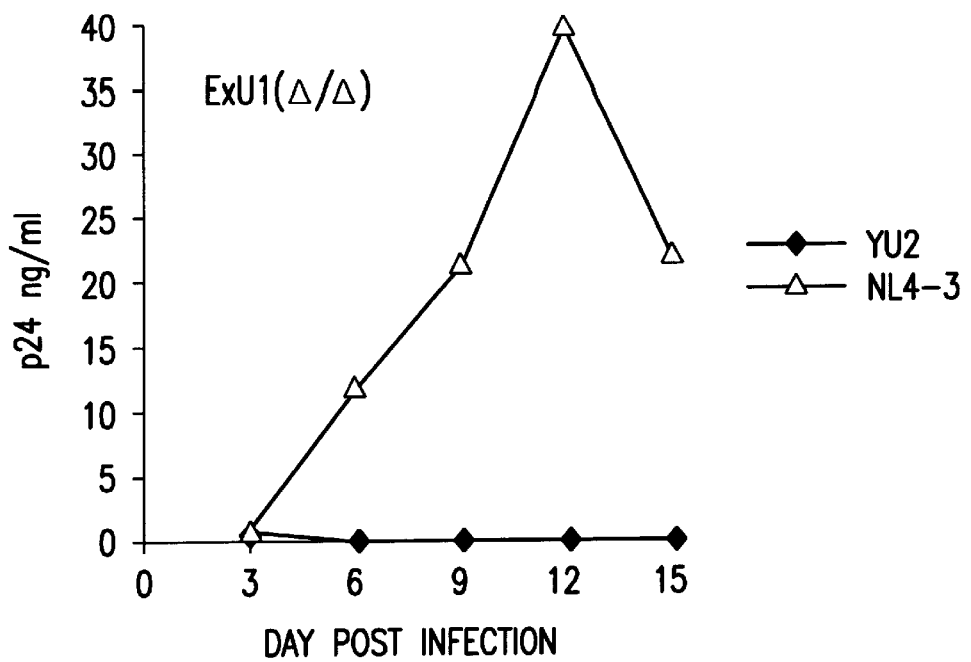
Figure 1D:
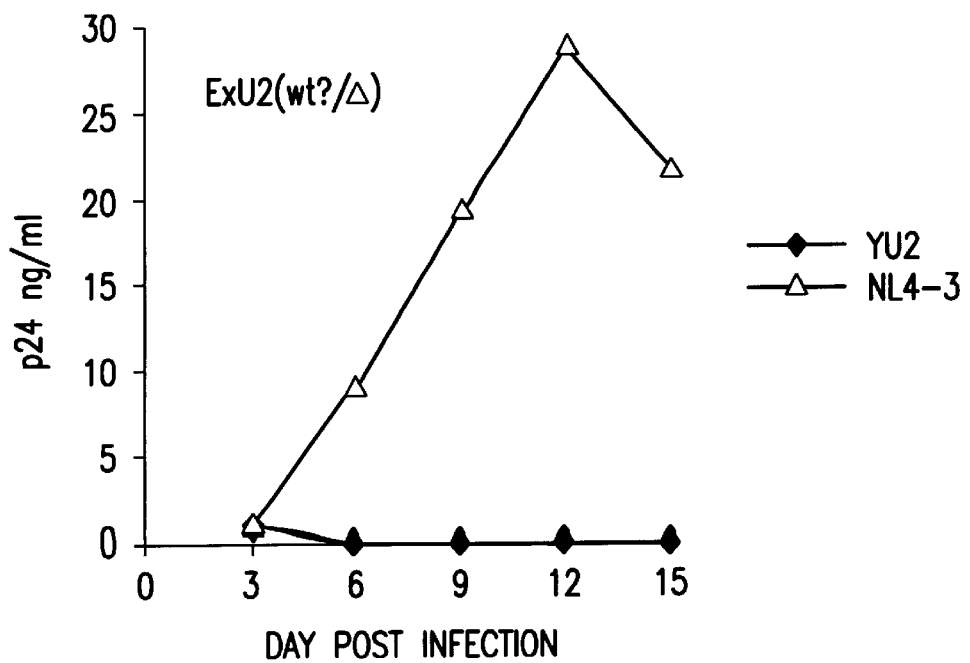

As expected, PBMC from all four individuals were readily infected by NL4-3 (FIGS. 1A–D). In contrast, both ExU1 and ExU2 were completely resistant to infection by YU2 (FIGS. 1C and 1D), while both UU1 and UU2 were susceptible (FIGS. 1A and 1B). Infection of both UU with YU2 could be inhibited by the HIV-suppressive chemokine RANTES, a ligand of CCR5 (FIGS. 1A and 1B).

The resistance of ExU2 PBMC to infection by CCR5-dependent viruses was not restricted to the YU2 molecular clone, as inoculation of PBMC from ExU2 with either two additional CCR5-dependent HIV viruses (JRCSF and BAL), as well as the HIV virus (V164) isolated from the seropositive partner of ExU2 (which, based on susceptibility to neutralization by RANTES, is CCR5 dependent), did not result in infection. Control PBMC from UU2 were, however, successfully infected by all three additional virus strains. Therefore, despite the fact that ExU2 was apparently heterozygous for the CCR5Δ32 mutation, he was resistant to infection by CCR5-dependent HIV-1.

The resistance of ExU2 PBMC to in vitro infection by CCR5-dependent viruses, together with his healthy clinical status despite an extensive history of sexual exposure, prompted the search for an alternative mutation in his non-deleted (?wt) allele. Therefore, the entire CCR5 gene of ExU2 was cloned, and the nucleotide sequence of both alleles was determined. The presence of the Δ32 deletion in one of the two alleles was confirmed. In addition, a single point mutation (T→A) at position 303 was found in the non-deleted allele, which is hereafter referred to as m303.

The remainder of the sequence (SEQ ID NO: 14) was otherwise identical to the wild-type gene (SEQ ID NO: 12; Samson et al., 1996, Biochemistry 35:3362). The m303 mutation generates a stop codon, which truncates the CCR5 at the 303 position, resulting in the loss of transmembrane regions 3–7 and the C-terminal cytoplasmic end of the molecule.

One explanation for why the m303 mutation together with the Δ32 deletion could account for the incapacity of macrophage-tropic HIV isolates to infect ExU2 PBMC would be that the variant proteins expressed by the two mutant alleles are non-functional. To explore this hypothesis, the wild type CCR5 and the two mutant alleles were each transfected into CD4+ human cells and tested for their capacity to generate a functional protein in an HIV envelope-mediated cell fusion assay, using CD4+ HeLa cells carrying an integrated HIV long terminal repeat ("LTR")-driven reporter gene (lacZ). Env-mediated cell fusion was assessed by measuring β-galactosidase generated from lacZ when HeLa cells transfected with defective provirus but expressing an HIV env gene were combined with CD4+, LTR/lacZ-containing HeLa cells transfected with nucleic acid encoding wild type CCR5, the CCR5m303 variant, or the CCR5Δ32 variant. If cell fusion via a CCR5/env interaction occurs, provirus encoded Tat protein from the env-bearing cells can activate the LTR sequence in the CCR5-bearing cells, and β-galactosidase expression will occur. The amount of β-galactosidase activity generated in the HeLa CD4+ cell depends on the induction of the HIV-1 LTR by the Tat protein and is an accurate measurement of env-mediated cell fusion.

As shown in FIG. 2, neither the CCR5m303 or the CCR5Δ32 variant were capable of generating a functional, fusion-permissive co-receptor, although wild-type CCR5-expressing CD4+ HeLa cells resulted in cell fusion. These results suggest that the resistance to infection of ExU2 was due to the absence of a functional CCR5 co-receptor.

Figure 3B:
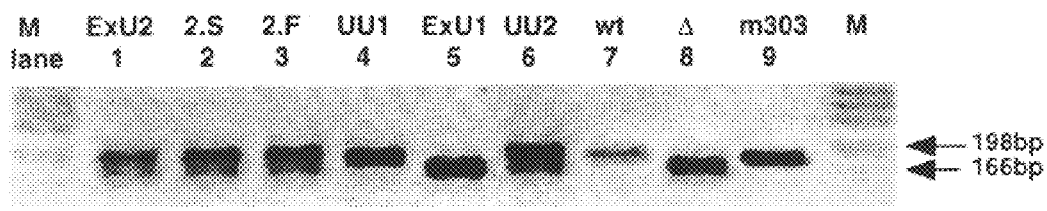

Next, we tested whether the CCR5 m303 mutant was a de novo mutation that arose in ExU2 or was inherited as a Mendelian trait. CCR5 genetic analysis and PBMC infection assays were performed in two immediate relatives of ExU2, namely, his father ("2.F") and his sister ("2.S"). When tested for the presence of the Δ32 mutation, it was found that both father and sister were heterozygous for this deletion (FIG. 3B).

Figure 3C:
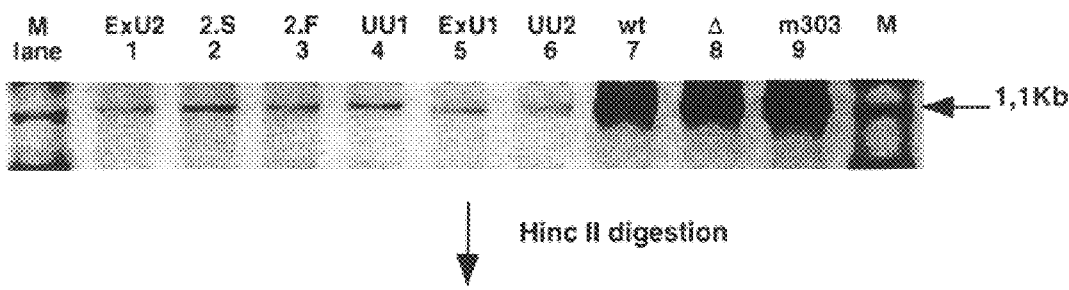
Figure 3D:
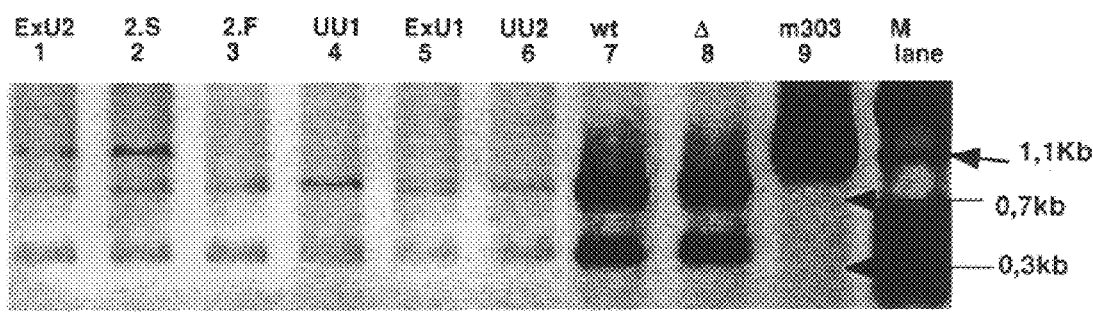

Next, we took advantage of the presence of a HincII restriction site at position 303 which is deleted by the T→A mutation, but present in the wild type gene (FIG. 3A) to screen genomic DNA from all individuals in this study. The entire CCR5 genomic sequences corresponding to ExU2, 2.S, 2.F, ExU1, UU1 and UU2 were amplified by PCR. FIG. 3C lanes 1–6 shows the uncleaved amplified DNA prepared from these six individuals, separated on a 1 percent agarose gel; all alleles showed similar patterns of migration. However, digestion with the restriction enzyme HincII generated different restriction patterns in the CCR5 alleles. Two distinct fragments of 0.7 and 0.3 kb were obtained from the genomic DNA of subjects who were either wild type (UU1), homozygous (ExU1) or heterozygous (UU2) for the Δ32 allele (FIG. 3D, lanes 4, 5 and 6). In contrast, the pattern of ExU2, which carries the m303 mutation on one allele, displayed an additional band migrating at an apparent size of 1.1 kb (FIG. 3D, lane 1).

To confirm these findings we analyzed cDNAs corresponding to CCR5 wild type, CCR5Δ32 and CCR5m303 alleles which had been characterized by nucleotide sequencing and cloned in a pCR3.1 plasmid. All of the cDNA products displayed the same restriction enzyme characteristics and migration pattern as those observed for CCR5 alleles directly amplified from genomic DNA (FIG. 3C lands 7, 8 and 9). HincII digestion of the three cloned genes generated two distinct fragments of 0.7 and 0.3 kb in the wild type and CCR5Δ32 plasmid clones (FIG. 3D lanes 7 and 8). In contrast, the CCR5m303 clone was not digested and displayed the original migration pattern of the entire CCR5 gene (1.1 kb) (FIG. 3D, lane 9). Upon digestion with HincII, genomic DNA from 2.S, but not 2.F, displayed a migration pattern identical to that of ExU2 (FIG. 3D, lanes 2 and 3), suggesting that the CCR5m303 mutation was inherited by both siblings from the mother as a single mendelian trait. Further genetic study was precluded because the mother was deceased. The presence of the CCR5Δ32 and the CCR5m303 alleles on cDNA from 2.S was confirmed by automatic nucleotide sequencing of the corresponding clones.

Since both ExU2 and 2.S carry the same CCR5 genetic trait, i.e., a combination of the CCR5m303 and the CCR5Δ32 mutant alleles, we compared their in vitro resistance to infection by a CCR5-dependent virus (YU2). In addition, we tested PBMC from 2.F, which carry the wild type and CCR5Δ32 alleles (but not CCR5m303). As would be expected based upon the lack of functionality of the two mutant alleles, 2.S PBMC displayed the same degree of resistance to infection as ExU2 PBMC whereas the 2.F PBMC were fully susceptible to infection with YU2 (FIG. 3A). All three individuals were susceptible to in vitro infection with NL4-3, the CXCR4-dependent virus (FIG. 3B).

7. EXAMPLE

Genetic Analysis

Genetic analysis of CCR5 from two unexposed uninfected (UU) individuals, two ExU (exposed uninfected) individuals, and two siblings of ExU2.

A fragment of CCR5-encoding DNA spanning the Δ32 deletion (hereafter, the Δ32 fragment) was amplified by PCR from genomic DNA prepared from PBMC using a pair of oligonucleotide primers having sequences as set forth in SEQ ID NOS: 1 and 2. PCR was conducted using 1 μg of genomic DNA and 0.2 mM dNTPs, 0.2 μM primers, and 1.25U of AmpliTaq Gold polymerase (PE Applied Biosystems, Branchburg, N.J.) for 35 cycles (94° C., 40 sec; 60° C., 40 sec; 72° C., 40 sec) after an initial 10 minute denaturation at 94° C. The resulting PCR products were separated on a 2 percent Nusieve agarose gel. Two fragments of 198 bp and 166 bp, corresponding to the wild-type and CCR5Δ32 alleles, were obtained.

PCR of genomic and plasmid DNA (200 ng) was conducted as above for 30 cycles (94° C., 1 min. 30 sec; 49° C. (for primers having SEQ ID NOS: 3 and 4; with pair of primers having SEQ ID NOS: 5 and 6, a temperature of 55° was used), 1 min.; 72° C., 1 min. 30 sec) after an initial 10 minute denaturation at 94° C.

The amplified products were cloned in a pCR3 vector using the TA cloning kit (Invitrogen, Leek, Netherlands). Automatic sequencing was performed using the same primers (ESGS, Research and Development Department, Evry, France). For analysis of restriction enzymes products of different CCR5 allels, the entire CCR5 cDNA was amplified using the same set of primers as set forth above, digested with HincII, and the fragments separated on an agarose gel.

Simultaneous detection of the CCR5Δ32 variant and the CCR5m303 variant were carried out by amplifying a portion of the CCR5 gene spanning both mutations using primers having the sequences set forth as SEQ ID NOS: 7 and 8. PCR was conducted using 1 μg of genomic DNA and 0.2 mM dNTPs, 0.2 μM primers, and 1.25 U of AmpliTAq Gold Polymerase (PE Applied Biosystems, Branchburg, N.J.) for 35 cycles (94° C., 40 sec; 56.5° C., 1 min; 72° C., 40 sec) after an initial 10 minute degradation at 94° C. The resulting PCR products were separated on a 2 percent Nusieve agarose gel. For analysis of restriction enzyme cleavage, the resulting PCR products were digested with Hinc II, and the fragments were separated on an agarose gel. The sizes of the amplified fragments and their restriction products were as follows: the wild-type gene was associated with an amplified fragment of 460 bp, which was apparently cleaved by HincII to yield two fragments of 66 and 394 bp; the CCR5Δ32 allele was associated with an amplified fragment of 428 bp, which was apparently cleaved by HincII to yield two fragments of 66 and 362 bp; and the CCR5m303 allele was associated with an amplified fragment of 460 bp which was not cleaved by HincII.

8. EXAMPLE

Cotransfection Trans-inhibition Experiments

HeLa P4 cells were cotransfected with different plasmids containing either CCR5 wild-type ("wt"), CCR5Δ32 ("Δ") or CCR5m303 ("m"), with DNA ratios of 1:1 (3 μg/3 μg). After 48 hours, a cell fusion assay was conducted with HeLa Ada cells. A β-galactosidase assay was performed, and the results expressed as the number of blue cells. The results, depicted in FIG. 5A, suggest that the negative interference of the mutant CCR5m303 is more effective than the Δ32 mutant.

In further experiments, U373 cells were co-transfected with different plasmids containing either CCR5 wild-type ("wt"), CCR5Δ32 ("Δ"), or CCR5m303 ("mn"), with various DNA ratios (1:1, 2 μg:2 μg; 1:3, 2 μg:6 μg; 3:1, 6 μg:2 μg). After 48 hours, a cell fusion assay was conducted with HeLa Ada cells. 24 hours later a CPRG lysis test assay was conducted and the results arc expressed with an OD value at 540 nm. The experiments show (FIG. 5B) that with CCR5m303, whatever the ratio, the same negative interference was observed. In contrast, a higher amount of wild-type plasmid could suppress the negative effect of the CCR5Δ32 variant. It therefore appears that the negative interference observed with CCR5Δ32 is dose-dependent, whereas the trans-inhibitory effect of the CCR5m303 variant is not.

Various publications are cited herein, the contents of which are hereby incorporated by reference in their entireties.

What is claimed is:

1. A purified and isolated nucleic acid encoding a purified CCR5 variant protein which comprises the first two transmembrane domains of wild type CCR5 but which lacks transmembrane domains 3, 4, 5, 6 and 7.

2. A purified and isolated nucleic acid encoding a purified CCR5 variant protein which comprises the first two transmembrane domains of wild type CCR5 but which lacks transmembrane domains 3, 4, 5, 6 and 7, and which comprises a portion having the amino acid sequence set forth as SEQ ID NO: 18, but which does not contain amino acid sequences as set forth in SEQ ID NOS: 19–23.

3. A purified and isolated nucleic acid encoding a purified CCR5 variant protein which comprises the first two transmembrane domains of wild type CCR5 but which lacks transmembrane domains 3, 4, 5, 6 and 7 and which is the CCR5 variant CCR5m303, having an amino acid sequence as set forth in SEQ ID NO: 15.

4. A purified and isolated nucleic acid which has the sequence set forth in SEQ ID NO: 14.

5. A purified and isolated nucleic acid encoding a purified CCR5 variant protein which comprises the first two transmembrane domains of wild type CCR5 but which lacks transmembrane domains 3, 4, 5, 6 and 7 and which is the CCR5 variant CCR5m303, having an amino acid sequence as set forth in SEQ ID NO: 15 and which is comprised together with heterologous amino acid sequence in a fusion protein.

6. The nucleic acid of claim 1 contained in a vector molecule.

7. The nucleic acid of claim 3 contained in a vector molecule.

8. The nucleic acid of claim 3 contained in a vector molecule.

9. The nucleic acid of claim 5 contained in a vector molecule.

10. A cell into which the nucleic acid of claim 1 has been introduced.

11. A cell into which the nucleic acid of claim 2 has been introduced.

12. A cell into which the nucleic acid of claim 3 has been introduced.

13. A cell into which the nucleic acid of claim 5 has been introduced.

* * * * *

UNITED STATES PATENT AND TRADEMARK OFFICE
CERTIFICATE OF CORRECTION

PATENT NO.   : 6,153,431  
DATED        : November 28, 2000  
INVENTOR(S)  : Beretta et al.

Page 1 of 1

It is certified that error appears in the above-identified patent and that said Letters Patent is hereby corrected as shown below:

<u>Column 34,</u>
Line 61, "claim 3" should read -- claim 2 --

Signed and Sealed this

Fourteenth Day of May, 2002

Attest:

JAMES E. ROGAN  
*Director of the United States Patent and Trademark Office*

*Attesting Officer*

UNITED STATES PATENT AND TRADEMARK OFFICE
CERTIFICATE OF CORRECTION

PATENT NO.    : 6,153,431
DATED         : November 28, 2000
INVENTOR(S)   : Beretta et al.

Page 1 of 1

It is certified that error appears in the above-identified patent and that said Letters Patent is hereby corrected as shown below:

<u>Title page,</u>
After Item [76], insert:

-- [73] Assignee: Fondation Modiale Recherche et Prevention Sida, Paris, France --.

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,153,431
DATED         : November 28, 2000
INVENTOR(S)   : Beretta et al.

It is certified that error appears in the above-identified patent and that said Letters Patent is hereby corrected as shown below:

<u>Title page,</u>
After Item [76], insert:

-- [73] Assignee: Fondation Mondiale Recherche et Prevention Sida, Paris, France --.

This certificate supersedes Certificate of Correction issued December 24, 2002

Signed and Sealed this

Twenty-fifth Day of March, 2003

JAMES E. ROGAN
*Director of the United States Patent and Trademark Office*

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PRIMER"

(xi) SEQUENCE DESCRIPTION: SEQ ID NO: 1:

GTCTTCATTA CACCTGCAGC TC                                            22

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PRIMER"

(xi) SEQUENCE DESCRIPTION: SEQ ID NO: 2:

GTGAAGATAA GCCTCACAGC C                                             21

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PRIMER"

(xi) SEQUENCE DESCRIPTION: SEQ ID NO: 3:

CCCAAGCTTA TGGATTATCA AGTG                                          24

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PRIMER"

(xi) SEQUENCE DESCRIPTION: SEQ ID NO: 4:

GCTCTAGATC ACAAGCCCAC AGA                                           23

(2) INFORMATION FOR SEQ ID NO: 5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
            (A) DESCRIPTION:    /desc = "PRIMER"

(xi) SEQUENCE DESCRIPTION: SEQ ID NO: 5:

GGGCAACTAA ATACAT                                                          16

(2) INFORMATION FOR SEQ ID NO: 6:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "PRIMER"

(xi) SEQUENCE DESCRIPTION: SEQ ID NO: 6:

GCACAACTCT GACTGG                                                          16

(2) INFORMATION FOR SEQ ID NO: 7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE:  other nucleic acid
            (A) DESCRIPTION:    /desc= "PRIMER"

(xi) SEQUENCE DESCRIPTION: SEQ ID NO: 7:

TCCTTCTTAC TGTCCCCTTC TGG                                                  23

(2) INFORMATION FOR SEQ ID NO: 8:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE:  other nucleic acid
            (A) DESCRIPTION:    /desc= "PRIMER"

(xi) SEQUENCE DESCRIPTION: SEQ ID NO: 8:

CCTGTGCCTC TTCTTCTCAT TTC                                                  23

(2) INFORMATION FOR SEQ ID NO: 9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE:  other nucleic acid
            (A) DESCRIPTION:    /desc= "PRIMER"

(xi) SEQUENCE DESCRIPTION: SEQ ID NO: 9:

AATACAATGT GTCAACTCTT G                                                    21

(2) INFORMATION FOR SEQ ID NO: 10:

(i) SEQUENCE CHARACTERISTICS:
            (A) LENGTH: 21 base pairs
            (B) TYPE: nucleic acid
            (C) STRANDEDNESS: single -continued (D) TOPOLOGY: linear (ii) MOLECULE TYPE: DNA (genomic)

(xi) SEQUENCE DESCRIPTION: SEQ ID NO: 10:

```
AATACAATGT GACAACTCTT G                                              21
```

(2) INFORMATION FOR SEQ ID NO: 11:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
TCCTTCTTAC TGTCCCCTTC TGGGCTCACT ATGCTGCCGC CCAGTGGGAC TTTGGAAATA     60

CAATGTGACA ACTCTTGACA GGGCTCTATT TTATAGGCTT CTTCTCTGGA ATCTTCTTCA    120

TCATCCTCCT GACAATCGAT AGGTACCTGG CTGTCGTCCA TGCTGTGTTT GCTTTAAAAG    180

CCAGGACGGT CACCTTTGGG GTGGTGACAA GTGTGATCAC TTGGGTGGTG GCTGTGTTTG    240

CGTCTCTCCC AGGAATCATC TTTACCAGAT CTCAAAAAGA AGGTCTTCAT TACACCTGCA    300

GCTCTCATTT TCCATACAGT CAGTATCAAT TCTGGAAGAA TTTCCAGACA TTAAAGATAG    360

TCATCTTGGG GCTGGTCCTG CCGCTGCTTG TCATGGTCAT CTGCTACTCG GGAATCCTAA    420

AAACTCTGCT TCGGTGTCGA AATGAGAAGA AGAGGCACAG G                        461
```

(2) INFORMATION FOR SEQ ID NO: 12:

(i) SEQUENCE CHARACTERISTICS:
        (A) LENGTH: 1376 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION:240..1298

(xi) SEQUENCE DESCRIPTION: SEQ ID NO: 12:

```
GAATTCCCCC AACAGAGCCA AGCTCTCCAT CTAGTGGACA GGGAAGCTAG CAGCAAACCT     60

TCCCTTCACT ACAAAACTTC ATTGCTTGGC CAAAAAGAGA GTTAATTCAA TGTAGACATC    120

TATGTAGGCA ATTAAAAACC TATTGATGTA TAAAACAGTT TGCATTCATG GAGGGCAACT    180

AAATACATTC TAGGACTTTA TAAAAGATCA CTTTTTATTT ATGCACAGGG TGGAACAAG    239

ATG GAT TAT CAA GTG TCA AGT CCA ATC TAT GAC ATC AAT TAT TAT ACA      287
Met Asp Tyr Gln Val Ser Ser Pro Ile Tyr Asp Ile Asn Tyr Tyr Thr
  1               5                  10                  15

TCG GAG CCC TGC CAA AAA ATC AAT GTG AAG CAA ATC GCA GCC CGC CTC      335
Ser Glu Pro Cys Gln Lys Ile Asn Val Lys Gln Ile Ala Ala Arg Leu
             20                  25                  30

CTG CCT CCG CTC TAC TCA CTG GTG TTC ATC TTT GGT TTT GTG GGC AAC      383
Leu Pro Pro Leu Tyr Ser Leu Val Phe Ile Phe Gly Phe Val Gly Asn
         35                  40                  45

ATG CTG GTC ATC CTC ATC CTG ATA AAC TGC AAA AGG CTG AAG AGC ATG      431
Met Leu Val Ile Leu Ile Leu Ile Asn Cys Lys Arg Leu Lys Ser Met
     50                  55                  60

ACT GAC ATC TAC CTG CTC AAC CTG GCC ATC TCT GAC CTG TTT TTC CTT      479
```

-continued

```
Thr Asp Ile Tyr Leu Leu Asn Leu Ala Ile Ser Asp Leu Phe Phe Leu
 65                  70                  75                  80

CTT ACT GTC CCC TTC TGG GCT CAC TAT GCT GCC GCC CAG TGG GAC TTT      527
Leu Thr Val Pro Phe Trp Ala His Tyr Ala Ala Ala Gln Trp Asp Phe
                 85                  90                  95

GGA AAT ACA ATG TGT CAA CTC TTG ACA GGG CTC TAT TTT ATA GGC TTC      575
Gly Asn Thr Met Cys Gln Leu Leu Thr Gly Leu Tyr Phe Ile Gly Phe
            100                 105                 110

TTC TCT GGA ATC TTC TTC ATC ATC CTC CTG ACA ATC GAT AGG TAC CTG      623
Phe Ser Gly Ile Phe Phe Ile Ile Leu Leu Thr Ile Asp Arg Tyr Leu
        115                 120                 125

GCT GTC GTC CAT GCT GTG TTT GCT TTA AAA GCC AGG ACG GTC ACC TTT      671
Ala Val Val His Ala Val Phe Ala Leu Lys Ala Arg Thr Val Thr Phe
    130                 135                 140

GGG GTG GTG ACA AGT GTG ATC ACT TGG GTG GTG GCT GTG TTT GCG TCT      719
Gly Val Val Thr Ser Val Ile Thr Trp Val Val Ala Val Phe Ala Ser
145                 150                 155                 160

CTC CCA GGA ATC ATC TTT ACC AGA TCT CAA AAA GAA GGT CTT CAT TAC      767
Leu Pro Gly Ile Ile Phe Thr Arg Ser Gln Lys Glu Gly Leu His Tyr
                165                 170                 175

ACC TGC AGC TCT CAT TTT CCA TAC AGT CAG TAT CAA TTC TGG AAG AAT      815
Thr Cys Ser Ser His Phe Pro Tyr Ser Gln Tyr Gln Phe Trp Lys Asn
            180                 185                 190

TTC CAG ACA TTA AAG ATA GTC ATC TTG GGG CTG GTC CTG CCG CTG CTT      863
Phe Gln Thr Leu Lys Ile Val Ile Leu Gly Leu Val Leu Pro Leu Leu
        195                 200                 205

GTC ATG GTC ATC TGC TAC TCG GGA ATC CTA AAA ACT CTG CTT CGG TGT      911
Val Met Val Ile Cys Tyr Ser Gly Ile Leu Lys Thr Leu Leu Arg Cys
    210                 215                 220

CGA AAT GAG AAG AAG AGG CAC AGG GCT GTG AGG CTT ATC TTC ACC ATC      959
Arg Asn Glu Lys Lys Arg His Arg Ala Val Arg Leu Ile Phe Thr Ile
225                 230                 235                 240

ATG ATT GTT TAT TTT CTC TTC TGG GCT CCC TAC AAC ATT GTC CTT CTC     1007
Met Ile Val Tyr Phe Leu Phe Trp Ala Pro Tyr Asn Ile Val Leu Leu
                245                 250                 255

CTG AAC ACC TTC CAG GAA TTC TTT GGC CTG AAT AAT TGC AGT AGC TCT     1055
Leu Asn Thr Phe Gln Glu Phe Phe Gly Leu Asn Asn Cys Ser Ser Ser
            260                 265                 270

AAC AGG TTG GAC CAA GCT ATG CAG GTG ACA GAG ACT CTT GGG ATG ACG     1103
Asn Arg Leu Asp Gln Ala Met Gln Val Thr Glu Thr Leu Gly Met Thr
        275                 280                 285

CAC TGC TGC ATC AAC CCC ATC ATC TAT GCC TTT GTC GGG GAG AAG TTC     1151
His Cys Cys Ile Asn Pro Ile Ile Tyr Ala Phe Val Gly Glu Lys Phe
    290                 295                 300

AGA AAC TAC CTC TTA GTC TTC TTC CAA AAG CAC ATT GCC AAA CGC TTC     1199
Arg Asn Tyr Leu Leu Val Phe Phe Gln Lys His Ile Ala Lys Arg Phe
305                 310                 315                 320

TGC AAA TGC TGT TCT ATT TTC CAG CAA GAG GCT CCC GAG CGA GCA AGC     1247
Cys Lys Cys Cys Ser Ile Phe Gln Gln Glu Ala Pro Glu Arg Ala Ser
                325                 330                 335

TCA GTT TAC ACC CGA TCC ACT GGG GAG CAG GAA ATA TCT GTG GGC TTG     1295
Ser Val Tyr Thr Arg Ser Thr Gly Glu Gln Glu Ile Ser Val Gly Leu
            340                 345                 350

TGA CACGGACTCA AGTGGGCTGG TGACCCAGTC AGAGTTGTGC ACATGGCTTA          1348
 *

GTTTTCATAC ACAGCCTGGG CTGGGGGT                                       1376
```

(2) INFORMATION FOR SEQ ID NO: 13:

(i) SEQUENCE CHARACTERISTICS:
           (A) LENGTH: 352 amino acids
           (B) TYPE: amino acid
           (D) TOPOLOGY: linear (ii) MOLECULE TYPE: protein (xi) SEQUENCE DESCRIPTION: SEQ ID NO: 13:

Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
             35                  40                  45

Met Leu Val Ile Leu Ile Leu Ile Asn Cys Lys Arg Leu Lys Ser Met
 50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350

(2) INFORMATION FOR SEQ ID NO: 14:

(i) SEQUENCE CHARACTERISTICS:

(A) LENGTH: 1071 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:7..309

(xi) SEQUENCE DESCRIPTION: SEQ ID NO: 14:

```
AAGCTT ATG GAT TAT CAA GTG TCA AGT CCA ATC TAT GAC ATC AAT TAT        48
       Met Asp Tyr Gln Val Ser Ser Pro Ile Tyr Asp Ile Asn Tyr
           355                 360                 365

TAT ACA TCG GAG CCC TGC CAA AAA ATC AAT GTG AAG CAA ATC GCA GCC       96
Tyr Thr Ser Glu Pro Cys Gln Lys Ile Asn Val Lys Gln Ile Ala Ala
                370                 375                 380

CGC CTC CTG CCT CCG CTC TAC TCA CTG GTG TTC ATC TTT GGT TTT GTG      144
Arg Leu Leu Pro Pro Leu Tyr Ser Leu Val Phe Ile Phe Gly Phe Val
385                 390                 395

GGC AAC ATG CTG GTC ATC CTC ATC CTG ATA AAC TGC AAA AGG CTG AAG      192
Gly Asn Met Leu Val Ile Leu Ile Leu Ile Asn Cys Lys Arg Leu Lys
400                 405                 410                 415

AGC ATG ACT GAC ATC TAC CTG CTC AAC CTG GCC ATC TCT GAC CTG TTT      240
Ser Met Thr Asp Ile Tyr Leu Leu Asn Leu Ala Ile Ser Asp Leu Phe
                420                 425                 430

TTC CTT CTT ACT GTC CCC TTC TGG GCT CAC TAT GCT GCC GCC CAG TGG      288
Phe Leu Leu Thr Val Pro Phe Trp Ala His Tyr Ala Ala Ala Gln Trp
                435                 440                 445

GAC TTT GGA AAT ACA ATG TGA CAACTCTTGA CAGGGCTCTA TTTTATAGGC         339
Asp Phe Gly Asn Thr Met  *
                450

TTCTTCTCTG GAATCTTCTT CATCATCCTC CTGACAATCG ATAGGTACCT GGCTGTCGTC    399

CATGCTGTGT TTGCTTTAAA AGCCAGGACG GTCACCTTTG GGGTGGTGAC AAGTGTGATC    459

ACTTGGGTGG TGGCTGTGTT TGCGTCTCTC CCAGGAATCA TCTTTACCAG ATCTCAAAAA    519

GAAGGTCTTC ATTACACCTG CAGCTCTCAT TTTCCATACA GTCAGTATCA ATTCTGGAAG    579

AATTTCCAGA CATTAAAGAT AGTCATCTTG GGGCTGGTCC TGCCGCTGCT TGTCATGGTC    639

ATCTGCTACT CGGGAATCCT AAAAACTCTG CTTCGGTGTC GAAATGAGAA GAAGAGGCAC    699

AGGGCTGTGA GGCTTATCTT CACCATCATG ATTGTTTATT TTCTCTTCTG GGCTCCCTAC    759

AACATTGTCC TTCTCCTGAA CACCTTCCAG GAATTCTTTG GCCTGAATAA TTGCAGTAGC    819

TCTAACAGGT TGGACCAAGC TATGCAGGTG ACAGAGACTC TTGGGATGAC GCACTGCTGC    879

ATCAACCCCA TCATCTATGC CTTTGTCGGG GAGAAGTTCA GAAACTACCT CTTAGTCTTC    939

TTCCAAAAGC ACATTGCCAA ACGCTTCTGC AAATGCTGTT CTATTTTCCA GCAAGAGGCT    999

CCCGAGCGAG CAAGCTCAGT TTACACCCGA TCCACTGGGG AGCAGGAAAT ATCTGTGGGC   1059

TTGTGATCTA GA                                                      1071
```

(2) INFORMATION FOR SEQ ID NO: 15:

(i) SEQUENCE CHARACTERISTICS:
        (A) LENGTH:  100 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
            35                  40                  45

Met Leu Val Ile Leu Ile Leu Ile Asn Cys Lys Arg Leu Lys Ser Met
        50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met
        100
```

(2) INFORMATION FOR SEQ ID NO: 16:

(i) SEQUENCE CHARACTERISTICS:
        (A) LENGTH: 1344 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION:240..887

(xi) SEQUENCE DESCRIPTION: SEQ ID NO: 16:

```
GAATTCCCCC AACAGAGCCA AGCTCTCCAT CTAGTGGACA GGGAAGCTAG CAGCAAACCT      60

TCCCTTCACT ACAAAACTTC ATTGCTTGGC CAAAAAGAGA GTTAATTCAA TGTAGACATC     120

TATGTAGGCA ATTAAAAACC TATTGATGTA TAAAACAGTT TGCATTCATG GAGGGCAACT     180

AAATACATTC TAGGACTTTA TAAAAGATCA CTTTTTATTT ATGCACAGGG TGGAACAAG      239

ATG GAT TAT CAA GTG TCA AGT CCA ATC TAT GAC ATC AAT TAT TAT ACA       287
Met Asp Tyr Gln Val Ser Ser Pro Ile Tyr Asp Ile Asn Tyr Tyr Thr
                105                  110                  115

TCG GAG CCC TGC CAA AAA ATC AAT GTG AAG CAA ATC GCA GCC CGC CTC       335
Ser Glu Pro Cys Gln Lys Ile Asn Val Lys Gln Ile Ala Ala Arg Leu
                120                  125                  130

CTG CCT CCG CTC TAC TCA CTG GTG TTC ATC TTT GGT TTT GTG GGC AAC       383
Leu Pro Pro Leu Tyr Ser Leu Val Phe Ile Phe Gly Phe Val Gly Asn
            135                  140                  145

ATG CTG GTC ATC CTC ATC CTG ATA AAC TGC AAA AGG CTG AAG AGC ATG       431
Met Leu Val Ile Leu Ile Leu Ile Asn Cys Lys Arg Leu Lys Ser Met
150                  155                  160                  165

ACT GAC ATC TAC CTG CTC AAC CTG GCC ATC TCT GAC CTG TTT TTC CTT       479
Thr Asp Ile Tyr Leu Leu Asn Leu Ala Ile Ser Asp Leu Phe Phe Leu
                170                  175                  180

CTT ACT GTC CCC TTC TGG GCT CAC TAT GCT GCC GCC CAG TGG GAC TTT       527
Leu Thr Val Pro Phe Trp Ala His Tyr Ala Ala Ala Gln Trp Asp Phe
                185                  190                  195

GGA AAT ACA ATG TGT CAA CTC TTG ACA GGG CTC TAT TTT ATA GGC TTC       575
Gly Asn Thr Met Cys Gln Leu Leu Thr Gly Leu Tyr Phe Ile Gly Phe
            200                  205                  210

TTC TCT GGA ATC TTC TTC ATC ATC CTC CTG ACA ATC GAT AGG TAC CTG       623
Phe Ser Gly Ile Phe Phe Ile Ile Leu Leu Thr Ile Asp Arg Tyr Leu
        215                  220                  225

GCT GTC GTC CAT GCT GTG TTT GCT TTA AAA GCC AGG ACG GTC ACC TTT       671
```

```
Ala Val Val His Ala Val Phe Ala Leu Lys Ala Arg Thr Val Thr Phe
230                 235                 240                 245

GGG GTG GTG ACA AGT GTG ATC ACT TGG GTG GTG GCT GTG TTT GCG TCT         719
Gly Val Val Thr Ser Val Ile Thr Trp Val Val Ala Val Phe Ala Ser
                250                 255                 260

CTC CCA GGA ATC ATC TTT ACC AGA TCT CAA AAA GAA GGT CTT CAT TAC         767
Leu Pro Gly Ile Ile Phe Thr Arg Ser Gln Lys Glu Gly Leu His Tyr
                265                 270                 275

ACC TGC AGC TCT CAT TTT CCA TAC ATT AAA GAT AGT CAT CTT GGG GCT         815
Thr Cys Ser Ser His Phe Pro Tyr Ile Lys Asp Ser His Leu Gly Ala
                280                 285                 290

GGT CCT GCC GCT GCT TGT CAT GGT CAT CTG CTA CTC GGG AAT CCT AAA         863
Gly Pro Ala Ala Ala Cys His Gly His Leu Leu Leu Gly Asn Pro Lys
295                 300                 305

AAC TCT GCT TCG GTG TCG AAA TGA GAAGAAGAGG CACAGGGCTG TGAGGCTTAT        917
Asn Ser Ala Ser Val Ser Lys *
310                 315

CTTCACCATC ATGATTGTTT ATTTTCTCTT CTGGGCTCCC TACAACATTG TCCTTCTCCT       977

GAACACCTTC AGGAATTCT TTGGCCTGAA TAATTGCAGT AGCTCTAACA GGTTGGACCA       1037

AGCTATGCAG GTGACAGAGA CTCTTGGGAT GACGCACTGC TGCATCAACC CCATCATCTA     1097

TGCCTTTGTC GGGGAGAAGT TCAGAAACTA CCTCTTAGTT TTCTTCCAAA AGCACATTGC     1157

CAAACGCTTC TGCAAATGCT GTTCTATTTT CCAGCAAGAG GCTCCCGAGC GAGCAAGCTC     1217

AGTTTACACC CGATCCACTG GGGAGCAGGA AATATCTGTG GGCTTGTGAC ACGGACTCAA     1277

GTGGGCTGGT GACCCAGTCA GAGTTGTGCA CATGGCTTAG TTTTCATACA CAGCCTGGGC     1337

TGGGGGT                                                               1344

(2) INFORMATION FOR SEQ ID NO: 17:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO: 17:

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
                35                  40                  45

Met Leu Val Ile Leu Ile Leu Ile Asn Cys Lys Arg Leu Lys Ser Met
            50                  55                  60

Thr Asp Ile Tyr Leu Leu Asn Leu Ala Ile Ser Asp Leu Phe Phe Leu
65              70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
            130                 135                 140

Gly Val Val Thr Ser Val Ile Thr Trp Val Val Ala Val Phe Ala Ser
```

```
145                 150                 155                 160
Leu Pro Gly Ile Ile Phe Thr Arg Ser Gln Lys Glu Gly Leu His Tyr
                165                 170                 175
Thr Cys Ser Ser His Phe Pro Tyr Ile Lys Asp Ser His Leu Gly Ala
            180                 185                 190
Gly Pro Ala Ala Ala Cys His Gly His Leu Leu Leu Gly Asn Pro Lys
        195                 200                 205
Asn Ser Ala Ser Val Ser Lys
210                 215
```

(2) INFORMATION FOR SEQ ID NO: 18:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Asp Tyr Gln Val Ser Ser Pro Ile Tyr Asp Ile Asn Tyr Tyr Thr
1               5                   10                  15
Ser Glu Pro Cys Gln Lys Ile Asn Val Lys Gln Ile Ala Ala Arg Leu
            20                  25                  30
Leu Pro Pro Leu Tyr Ser Leu Val Phe Ile Phe Gly Phe Val Gly Asn
        35                  40                  45
Met Leu Val Ile Leu Ile Leu Ile Asn Cys Lys Arg Leu Lys Ser Met
    50                  55                  60
Thr Asp Ile Tyr Leu Leu Asn Leu Ala Ile Ser Asp Leu Phe Phe Leu
65                  70                  75                  80
Leu Thr Val Pro Phe Trp Ala
                85
```

(2) INFORMATION FOR SEQ ID NO: 19:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO: 19:

```
Leu Leu Thr Gly Leu Tyr Phe Ile Gly Phe Phe Ser Gly Ile Phe Phe
                5                   10                  15
Ile Ile Leu Leu Thr Ile
            20
```

(2) INFORMATION FOR SEQ ID NO: 20:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 20:

```
Val Thr Phe Gly Val Val Thr Ser Val Ile Thr Trp Val Val Ala Val
                5                   10                  15
Phe Ala Ser Leu Pro Gly Ile Ile Phe Thr
            20                  25
```

(2) INFORMATION FOR SEQ ID NO:21:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO: 21:

Ile Leu Gly Leu Val Leu Pro Leu Leu Val Met Val Ile Cys Tyr Ser
                  5                  10                  15

Gly Ile Leu Lys Thr Leu Leu Arg
             20

(2) INFORMATION FOR SEQ ID NO: 22:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO: 22:

Leu Ile Phe Thr Ile Met Ile Val Tyr Phe Leu Phe Trp Ala Pro Tyr
                  5                  10                  15

Asn Ile Val Leu Leu Leu Asn Thr Phe
             20                  25

(2) INFORMATION FOR SEQ ID NO: 23:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 23:

Leu Asp Gln Ala Met Gln Val Thr Glu Thr Leu Gly Met Thr His Cys
                  5                  10                  15

Cys Ile Asn Pro Ile Ile Tyr Ala Phe Val Gly
             20                  25